(12) United States Patent
Yamagata et al.

(10) Patent No.: US 10,080,508 B2
(45) Date of Patent: Sep. 25, 2018

(54) MAGNETIC RESONANCE IMAGING APPARATUS AND IMAGE PROCESSING APPARATUS

(71) Applicant: TOSHIBA MEDICAL SYSTEMS CORPORATION, Otawara-shi (JP)

(72) Inventors: Hitoshi Yamagata, Otawara (JP); Masao Yui, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/254,108

(22) Filed: Sep. 1, 2016

(65) Prior Publication Data

US 2017/0071497 A1    Mar. 16, 2017

(30) Foreign Application Priority Data

Sep. 10, 2015   (JP) .................................. 2015-178613
Jul. 1, 2016    (JP) .................................. 2016-131795

(51) Int. Cl.
| | |
|---|---|
| *G06K 9/00* | (2006.01) |
| *A61B 5/055* | (2006.01) |
| *G06T 7/00* | (2017.01) |
| *G01R 33/48* | (2006.01) |
| *A61B 5/05* | (2006.01) |
| *A61B 5/00* | (2006.01) |

(52) U.S. Cl.
CPC .......... *A61B 5/055* (2013.01); *G01R 33/4806* (2013.01); *G06T 7/0012* (2013.01); *G06T 7/0081* (2013.01); *A61B 5/0042* (2013.01); *A61B 5/743* (2013.01); *A61B 2576/026* (2013.01); *G06T 2207/10088* (2013.01); *G06T 2207/20112* (2013.01); *G06T 2207/30016* (2013.01)

(58) Field of Classification Search
USPC ........ 382/100, 103, 106–107, 128–134, 154, 382/162, 168, 173, 181, 195, 199, 219, 382/232, 254, 274, 276, 286–291, 305, 382/312; 345/204; 324/309; 703/2; 600/410

See application file for complete search history.

(56) References Cited

U.S. PATENT DOCUMENTS 9,788,784 B2 * 10/2017 Reiman ................ A61B 5/4848
2009/0093706 A1 * 4/2009 Zhang ................... A61B 5/055
                                                                600/410

(Continued)

OTHER PUBLICATIONS

Juan Zhou, et al., "Predicting Regional Neurodegeneration from the Healthy Brain Functional Connectome", Neuron, 2012, 12 pgs.

(Continued)

*Primary Examiner* — Seyed Azarian
(74) *Attorney, Agent, or Firm* — Oblon, McClelland, Maier & Neustadt, L.L.P.

(57) ABSTRACT

A magnetic resonance imaging apparatus according to an embodiment includes processing circuitry. The processing circuitry is configured to perform control to display a matrix representing inter-regional connectivity between a plurality of regions in a brain. The processing circuitry is configured to perform, based on an attention degree set to each of the regions, control to selectively display part of a plurality of regions arranged along a first axis of the matrix.

11 Claims, 31 Drawing Sheets

(56) References Cited

U.S. PATENT DOCUMENTS

2010/0049482 A1* 2/2010 He .................. A61B 5/048
  703/2
2012/0249498 A1* 10/2012 Sugiyama .............. A61B 5/055
  345/204
2012/0280686 A1* 11/2012 White .............. G01R 33/56341
  324/309

OTHER PUBLICATIONS

Susumu Mori, et al., "Atlas-Based Neuroinformatics via MRI: Harnessing Information from Past Clinical Cases and Quantitative Image Analysis for Patient Care", Annual Review of Biomedical Engineering, vol. 15, 2013, 22 pgs.

* cited by examiner

FIG.4

| lentiform nucleus (LENTIFORM NUCLEUS) | | basal ganglia (BGN) (BASAL GANGLIA) | | | | | hippocampus (HIPPOCAMPUS) | | limbic system (LIMBIC SYSTEM) | | |
|---|---|---|---|---|---|---|---|---|---|---|---|
| globus pallidus: GP (GLOBUS PALLIDUS) | PUTA-MEN | CAU-DATE NU-CLEUS | SUB-STAN-TIA NIGRA | SUB-STAN-TIA NIGRA PARS COM-PACTA | ACCUM-BENS NU-CLEUS | NU-CLEUS BASALIS OF MEYNERT | AMMON'S HORN (HIPPO-CAMPUS PROPER) | DEN-TATE GYRUS | PARAHIPPO-CAMPAL GYRUS | EN-TORHINAL AREA | AMYG-DALA | CINGU-LATE GYRUS |

FIG.5

| g1 | g2 | g3 | g4 | g5 | g6 | g7 | g8 | g9 | g10 | g11 | g12 | g13 | g14 | g15 | g16 | g17 | g18 | g19 | g20 |
|----|----|----|----|----|----|----|----|----|-----|-----|-----|-----|-----|-----|-----|-----|-----|-----|-----|
| sub-region 1 | | | | | | | | | | | | | | | | | | | |
| region 1 | | | | | | | region 2 | | | | | | | region 3 | | | | | |
| right hemisphere | | | | | | | | | | | | | | | | | | | |

| g1 | g2 | g3 | g4 | g5 | g6 | g7 | g8 | g9 | g10 | g11 | g12 | g13 | g14 | g15 | g16 | g17 | g18 | g19 | g20 |
|----|----|----|----|----|----|----|----|----|-----|-----|-----|-----|-----|-----|-----|-----|-----|-----|-----|
| sub-region 1 | | | | | | | | | | | | | | | | | | | |
| region 1 | | | | | | | region 2 | | | | | | | region 3 | | | | | |
| left hemisphere | | | | | | | | | | | | | | | | | | | |

FIG.6

| level 1: hemisphere | hemisphere 1 | | | | | | | | | | | | | |
|---|---|---|---|---|---|---|---|---|---|---|---|---|---|---|
| level 2: lobe | lobe 1 | | | | | | | | | lobe 2 | | | | |
| level 3: gyrus | gyrus 1 | | | gyrus 2 | | | | | | gyrus 3 | | | | |
| level 4: tissue | gray matter | | | | | | | | | white matter | | | | |
| level 5: cell type | cell type 1 | | | | | | | | | cell type 2 | | | | |
| level 6: sub-cell type | g1 | g2 | g3 | g4 | g5 | g6 | g7 | g8 | g9 | g10 | g11 | g12 | g13 | g14 |

FIG.11

| 0 | 0 | 0 | 1 | 0 | 0 | 3 | 4 | 2 | 0 | 0 | 1 | 3 | 4 | 2 | 0 | 3 | 3 | 3 | 1 | 1 | 1 | 1 | 1 |
|---|---|---|---|---|---|---|---|---|---|---|---|---|---|---|---|---|---|---|---|---|---|---|---|
| g1 | g2 | g3 | g4 | g5 | g6 | g7 | g8 | g9 | g10 | g11 | g12 | g13 | g14 | g15 | g16 | g17 | g18 | g19 | g20 | f1 | f2 | f3 | f4 | f5 | f6 | f7 | f8 | sub-region 1 | region 1 | region 2 | region 3 | cluster 1 | cluster 2 left hemisphere

| 0 | 0 | 0 | 2 | 1 | 0 | 0 | 3 | 4 | 4 | 2 | 0 | 0 | 1 | 3 | 4 | 2 | 0 | 4 | 4 | 4 | 3 | 3 | 3 | 3 | 3 | 3 |
|---|---|---|---|---|---|---|---|---|---|---|---|---|---|---|---|---|---|---|---|---|---|---|---|---|---|---|
| g1 | g2 | g3 | g4 | g5 | g6 | g7 | g8 | g9 | g10 | g11 | g12 | g13 | g14 | g15 | g16 | g17 | g18 | g19 | g20 | f1 | f2 | f3 | f4 | f5 | f6 | f7 | f8 | sub-region 1 | region 1 | region 2 | region 3 | cluster 1 | cluster 2 right hemisphere

MAGNETIC RESONANCE IMAGING APPARATUS AND IMAGE PROCESSING APPARATUS

CROSS-REFERENCE TO RELATED APPLICATIONS

This application is based upon and claims the benefit of priority from Japanese Patent Application No. 2015-178613, filed on Sep. 10, 2015, and Japanese Patent Application No. 2016-131795, filed on Jul. 1, 2016; the entire contents of which are incorporated herein by reference.

FIELD

Embodiments described herein relate generally to a magnetic resonance imaging apparatus and an image processing apparatus.

BACKGROUND

Recent ongoing researches in the field of neuroscience relate to brain functional localized regions and their inter-regional connectivity therebetween based on images acquired by a magnetic resonance imaging apparatus. For example, a disclosed method determines any disease by analyzing a difference in a predetermined parameter such as an intensity value of an image from the normal brain for each brain functional localized region.

BRIEF DESCRIPTION OF THE DRAWINGS

FIG. 4 is a diagram illustrating a hierarchical structure of a cortex region;

FIG. 5 is a diagram illustrating a generalized example of the hierarchical structure of the cortex region;

FIG. 6 is a diagram illustrating a generalized example of a hierarchical structure of the cortex region and a white matter region;

FIG. 11 is a diagram illustrating an exemplary DSAM according to the first embodiment;

DETAILED DESCRIPTION

A magnetic resonance imaging (MRI) apparatus according to an embodiment includes processing circuitry. The processing circuitry is configured to perform control to display a matrix representing inter-regional connectivity between a plurality of regions in a brain. The processing circuitry is configured to perform, based on an attention degree set to each of the regions, control to selectively display part of a plurality of regions arranged along a first axis of the matrix.

First Embodiment

Figure 1:
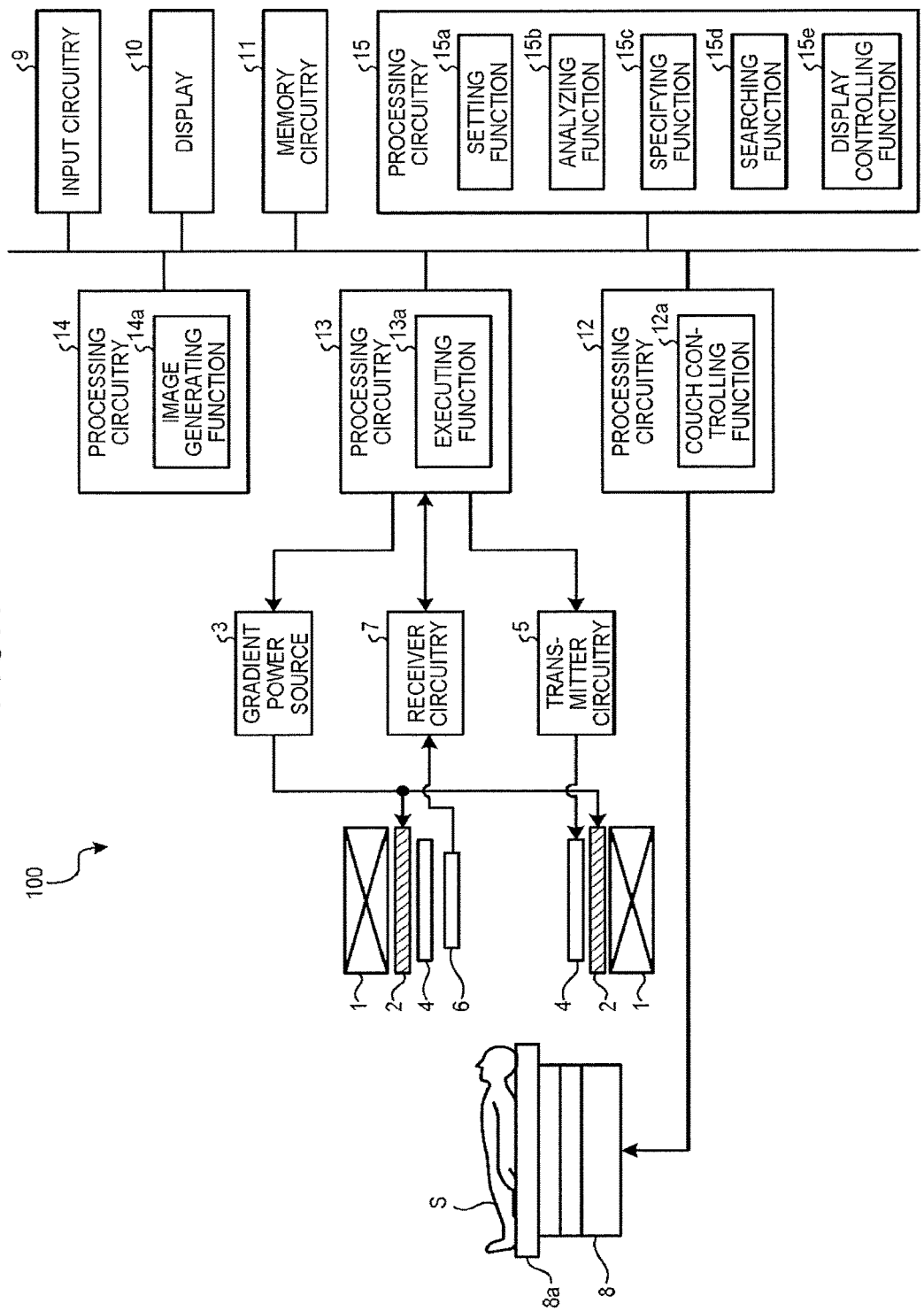
FIG. 1 is a diagram illustrating an exemplary configuration of an MRI apparatus according to a first embodiment.

FIG. 1 is a diagram illustrating an exemplary configuration of an MRI apparatus 100 according to a first embodiment. For example, as illustrated in FIG. 1, the MRI apparatus 100 includes a static magnetic magnet 1, a gradient coil 2, a gradient power source 3, a transmitter coil 4, transmitter circuitry 5, a receiver coil 6, receiver circuitry 7, a couch 8, input circuitry 9, a display 10, memory circuitry 11, processing circuitry 12, processing circuitry 13, processing circuitry 14, and processing circuitry 15.

The static magnetic magnet 1 substantially has a hollow cylinder shape (including a cylinder having an ellipse section orthogonal to its central axis), and is configured to generate a homogeneous static magnetic field in an imaging space formed inside the static magnetic magnet 1. Examples of the static magnetic magnet 1 include a permanent magnet and a superconducting magnet.

The gradient coil 2 substantially has a hollow cylinder shape (including a cylinder having an ellipse section orthogonal to its central axis), and is arranged inside the static magnetic magnet 1. The gradient coil 2 includes three coils that generate gradient magnetic fields along mutually orthogonal x, y, and z axes. The x, y and z axes span an apparatus coordinate system intrinsic to the MRI apparatus 100. For example, the direction of the x axis is set to the vertical direction, and the direction of the y axis is set to the horizontal direction. The direction of the z axis is set to the direction of the magnetic flux of a static magnetic field generated by the static magnetic magnet 1.

The gradient power source 3 generates gradient magnetic fields along the respective x, y, and z axes in the imaging space by supplying current individually to the three coils included in the gradient coil 2. Generating the gradient magnetic fields along the x, y, and z axes as appropriate enables generation of gradient magnetic fields in a readout direction, a phase encoding direction, and a slice direction, respectively, which are mutually orthogonal. Axes along the readout direction, the phase encode direction, and the slice direction span a logical coordinate system for defining a slice region or a volume region as an imaging target. In the following, a gradient magnetic field in the readout direction is referred to as a readout gradient magnetic field, a gradient magnetic field in the phase encoding direction is referred to as a phase encoding gradient magnetic field, and a gradient magnetic field in the slice direction is referred to as a slice gradient magnetic field.

These gradient magnetic fields are superimposed on the static magnetic field generated by the static magnetic magnet 1 and are used to add spatial positional information to a magnetic resonance (MR) signal. Specifically, the readout gradient magnetic field adds positional information in the readout direction to the MR signal by changing the frequency of the MR signal in accordance with a position in the readout direction. The phase encoding gradient magnetic field adds positional information in the phase encoding direction to the MR signal by changing the phase of the MR signal in the phase encoding direction. When the imaging space is a slice region, the slice gradient magnetic field is used to determine the direction, thickness and position of the slice region and the number of slices. When the imaging space is a volume region, the slice gradient magnetic field adds positional information in the slice direction to the MR signal by changing the phase of the MR signal in accordance with a position in the slice direction.

The transmitter coil 4 substantially has a hollow cylinder shape (including a cylinder having an ellipse section orthogonal to its central axis), and is arranged inside the gradient coil 2. The transmitter coil 4 applies a radio frequency (RF) pulse output from the transmitter circuitry 5 to the imaging space.

The transmitter circuitry 5 outputs the RF pulse corresponding to a Larmor frequency to the transmitter coil 4. For example, the transmitter circuitry 5 includes oscillation circuitry, phase selection circuitry, frequency conversion circuitry, amplitude modulation circuitry, and RF amplification circuitry. The oscillation circuitry generates an RF pulse having a resonant frequency intrinsic to a target nucleus placed in a static magnetic field. The phase selection circuitry selects the phase of the RF pulse output from the oscillation circuitry. The frequency conversion circuitry converts the frequency of the RF pulse output from the phase selection circuitry. The amplitude modulation circuitry modulates the amplitude of the RF pulse output from the frequency conversion circuitry according to, for example, a sinc function. The RF amplification circuitry amplifies the RF pulse output from the amplitude modulation circuitry and outputs the amplified RF pulse to the transmitter coil 4.

The receiver coil 6 is an RF coil configured to receive an MR signal emitted from a subject S. Specifically, the receiver coil 6 is mounted on the subject S placed in the imaging space and is configured to receive the MR signal emitted from the subject S in response to an RF magnetic field applied by the transmitter coil 4. The receiver coil 6 outputs the received MR signal to the receiver circuitry 7. For example, a dedicated coil is used as the receiver coil 6 for each site of an imaging target. Examples of this dedicated coil include receiver coils for the head, neck, shoulders, chest, abdomen, legs, and spine.

The receiver circuitry 7 generates MR signal data based on the MR signal output from the receiver coil 6, and outputs the generated MR signal data to the processing circuitry 13. For example, the receiver circuitry 7 includes a selection circuitry, a preamplification circuitry, a phase detection circuitry, and an analog-digital conversion circuitry. The selection circuitry selectively inputs the MR signal output from the receiver coil 6. The preamplification circuitry amplifies the MR signal output from the selection circuitry. The phase detection circuitry detects the phase of the MR signal output from the preamplification circuitry. The analog digital conversion circuitry generates the MR signal data by converting an analog signal output from the phase detection circuitry into a digital signal, and outputs the generated MR signal data to the processing circuitry 13.

Although the following describes an example in which the transmitter coil 4 applies an RF pulse and the receiver coil 6 receives an MR signal, the transmitter coil and the receiver coil are not limited to this configuration. For example, the transmitter coil 4 may further have a receiving function to receive an MR signal. The receiver coil 6 may further have a transmitting function to apply an RF magnetic field. In a case in which the transmitter coil 4 has the receiving function, the receiver circuitry 7 generates MR signal data also from an MR signal received by the transmitter coil 4. In another case in which the receiver coil 6 has the transmitting function, the transmitter circuitry 5 outputs an RF pulse also to the receiver coil 6.

The couch 8 is provided with a couchtop 8a on which the subject S is placed, and is used to insert the couchtop 8a into the imaging space formed inside the static magnetic magnet 1 and the gradient coil 2 at imaging of the subject S. For example, the couch 8 is installed such that its longitudinal direction is parallel to the central axis of the static magnetic magnet 1.

The input circuitry 9 receives, from an operator, an operation to input various kinds of instructions and information. Specifically, the input circuitry 9 is connected with the processing circuitry 15 and is configured to convert the input operation received from the operator into an electric signal and output the electric signal to the processing circuitry 15. Examples of the input circuitry 9 include a trackball, a switch button, a mouse, a keyboard, and a touch panel.

The display 10 displays various kinds of information and images. Specifically, the display 10 is connected with the processing circuitry 15 and is configured to convert data of various kinds of information and images transmitted from the processing circuitry 15 into display electric signals and output these display electric signals. Examples of the display 10 include a liquid crystal monitor, a cathode ray tube (CRT) monitor, and a touch panel.

The memory circuitry 11 stores therein various kinds of data. Specifically, the memory circuitry 11 stores therein MR signal data and image data for each subject S. Examples of the memory circuitry 11 include a semiconductor memory element such as a random access memory (RAM) or a flash memory, a hard disk, and an optical disk.

The processing circuitry 12 has a couch controlling function 12a. Specifically, the couch controlling function 12a is connected with the couch 8 and is configured to output a control electric signal to the couch 8 to control operation of the couch 8. For example, the couch controlling function 12a receives, from the operator through the input circuitry 9, an instruction to move the couchtop 8a in the longitudinal direction, the vertical direction, or the lateral direction, and operates a mechanism of the couch 8 for driving the couchtop 8a to move the couchtop 8a in accordance with the received instruction. For example, the processing circuitry 12 is a processor.

The processing circuitry 13 has an executing function 13a. Specifically, the executing function 13a executes various kinds of pulse sequences. Specifically, the executing function 13a drives the gradient power source 3, the transmitter circuitry 5, and the receiver circuitry 7 based on sequence execution data output from the processing circuitry 15 so as to execute various kinds of pulse sequences. For example, the processing circuitry 13 is a processor.

The sequence execution data is information that defines a pulse sequence indicating a procedure of collecting MR signal data. Specifically, the sequence execution data is information that defines a timing at which the gradient power source 3 supplies current to the gradient coil 2, the intensity of the supplied current, the intensity of RF pulse current supplied to the transmitter coil 4 by the transmitter circuitry 5 and the supply timing thereof, and a detection timing at which the receiver circuitry 7 detects an MR signal.

By executing the various kinds of pulse sequences, the executing function 13a receives MR signal data from the receiver circuitry 7 and stores the received MR signal data in the memory circuitry 11. A collection of the MR signal data received by the executing function 13a is two-dimensionally or three-dimensionally arrayed in accordance with the positional information added by the readout gradient magnetic field, the phase encoding gradient magnetic field, and the slice gradient magnetic field described above, and is stored as data that spans the k space in the memory circuitry 11.

The processing circuitry 14 has an image generating function 14a. For example, the processing circuitry 14 is a processor. The image generating function 14a generates an image based on the MR signal data stored in the memory circuitry 11. Specifically, the image generating function 14a reads out the MR signal data stored in the memory circuitry 11 by the executing function 13a, and generates an image by providing the read MR signal data with post-processing, in other words, reconstruction processing such as a Fourier transform. The image generating function 14a stores image data of the generated image in the memory circuitry 11.

The processing circuitry 15 performs entire control of the MRI apparatus 100 by controlling each component included in the MRI apparatus 100. For example, the processing circuitry 15 is a processor. For example, the processing circuitry 15 receives inputs of various kinds of parameters related to a pulse sequence from the operator through the input circuitry 9, and generates sequence execution data based on the received parameters. Then, the processing circuitry 15 transmits the generated sequence execution data to the processing circuitry 13 so as to execute various kinds of pulse sequences. For example, the processing circuitry 15 reads out, from the memory circuitry 11, image data of an image requested by the operator and outputs the read image to the display 10.

The exemplary configuration of the MRI apparatus 100 according to the present embodiment is described above. The MRI apparatus 100 according to the present embodiment with such a configuration is used for image analysis on a plurality of regions in a brain.

The regions in the brain are localized regions of the brain for a purpose. For example, the regions in brain are functionally or anatomically localized regions of the brain. The following describes an example in which the regions in the brain are a plurality of brain functional localized regions (also simply referred to as localized regions), but the embodiment is not limited thereto.

Ongoing recent researches in the field of neuroscience relate to brain functional localized regions and inter-regional connectivity therebetween using images acquired by an MRI apparatus. For example, a disclosed method determines any disease by analyzing a difference in a predetermined parameter such as an intensity value of an image from a normal brain for each brain functional localized region.

However, such a method is mainly purposed for study and is not logically understandable in clinical application. The method does not provide a framework for practical clinical application in accordance with a diagnosis purpose, in other words, definitive diagnosis and screening, in particular.

Thus, a framework is needed that is easily understandable by a general neuroradiologist or physician and uses information on brain functional localized regions and their inter-regional connectivity therebetween in accordance with a diagnosis purpose.

A mechanism related to this framework, which is easily understandable by a general neuroradiologist or physician and uses information on brain functional localized regions and their inter-regional connectivity therebetween in accordance with a diagnosis purpose, is needed to present its diagnosis information in an easily understandable manner.

For these reasons, the MRI apparatus 100 according to the present embodiment is configured to be capable of supporting an image analysis on a plurality of regions in the brain.

Specifically, in the present embodiment, the memory circuitry 11 stores therein information indicating a matrix representing inter-regional connectivity between a plurality of brain functional localized regions. The following describes a hierarchical structure of brain functional localized regions, fiber-clusters, and cortex regions, followed by a detailed description of the matrix stored in the memory circuitry 11.

Figure 2:
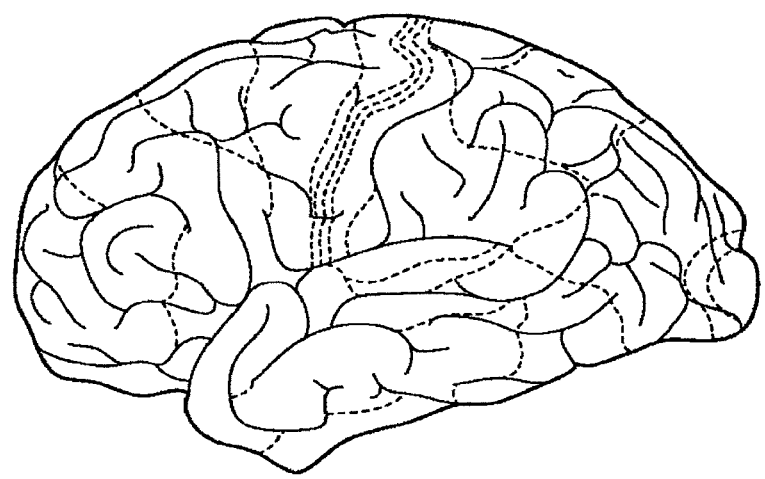
FIG. 2 is a diagram illustrating brain functional localized regions.

FIG. 2 is a diagram illustrating brain functional localized regions. For example, as illustrated in FIG. 2, a brain is divided into a plurality of brain functional localized regions (regions divided by dashed lines and solid lines illustrated in FIG. 2). Each brain functional localized region includes a cortex region and a white matter region. The cortex region is the region of a cortex (also referred to as gray matter) including a nerve cell, covering the surface of the brain. The white matter region is the region of a white matter (also referred to as subcortical component) containing nerve fibers, and is present inside the brain. A minimum unit of the cortex region is referred to as a gyrus. A collection of gyri is, for example, a cortex, and examples of division units in a further macro scale include a frontal lobe, an occipital lobe, a temporal lobe, and a parietal lobe.

Figure 3:
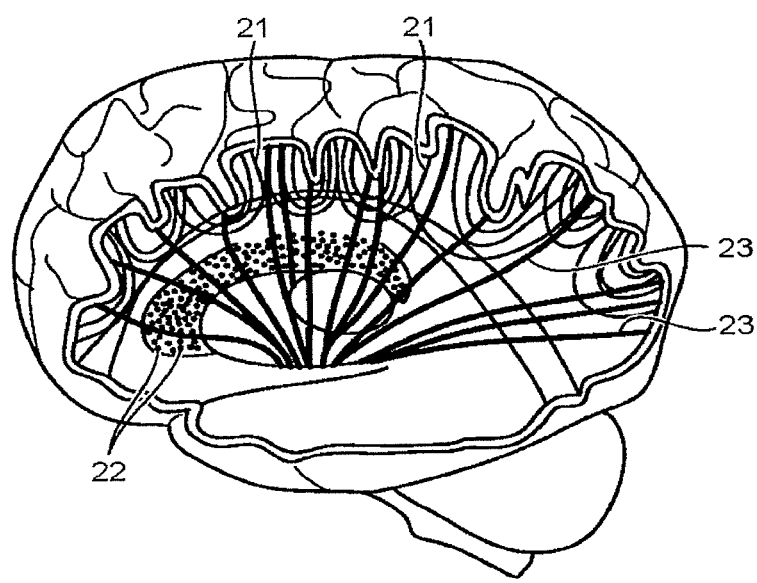
FIG. 3 is a diagram illustrating fiber-clusters.

FIG. 3 is a diagram illustrating fiber-clusters. A fiber-cluster is a collection of nerve fibers. FIG. 3 illustrates nerve fibers coupled with brain functional localized regions in a skull. A nerve fiber (nerve) typically refers to an axon bundle (bundle) as a collection of axons each extending from a nerve cell. As illustrated in FIG. 3, examples of the nerve fiber include an association fiber (AF) 21, a commissural fiber (CF) 22, and a projection fiber (PF) 23. The association fiber 21 is a fiber connecting brain functional localized regions included in the same hemisphere, and is classified into a short association fiber or a long association fiber. The commissural fiber 22 is a fiber connecting, through the corpus callosum, a brain functional localized region included in the left hemisphere of the brain and a brain functional localized region included in the right hemisphere of the brain. The projection fiber 23 is a fiber connecting a cortex region and a white matter region, and is classified as an efferent projection fiber from the cortex region toward the white matter region or an afferent projection fiber from the white matter region toward the cortex region. The projection fiber 23 is a nerve fiber coupling a brain functional localized region with a sensory apparatus (input) or a locomotor apparatus (output). Part of the projection fiber 23 is coupled with the sensory apparatus or the locomotor apparatus through a thalamus and an internal capsule serving as relay structures.

These nerve fibers basically pass through some minor structures (minor functional structures) in a white matter region, such as a thalamus and an internal capsule described above. Thus, in the following, a gyrus is defined as a minimum unit of a brain functional localized region including a cortex region and regions of some minor structures (minor functional structure) in a white matter region.

FIG. 4 is a diagram illustrating a hierarchical structure of the cortex region. Typically, a gyrus as the minimum unit of the cortex region is functionally or anatomically classified in one of a plurality of categories. For example, as illustrated in FIG. 4, the kinds of gyri include globus pallidus, putamen, caudate nucleus, substantia nigra, substantia nigra pars compacta, accumbens nucleus, nucleus basalis of Meynert, ammon's horn, dentate gyrus, parahippocampal gyrus, entorhinal area, amygdala, and cingulate gyrus. Globus pallidus and putamen are classified in lentiform nucleus, and ammon's horn and dentate gyrus are classified in hippocampus. Globus pallidus to nucleus basalis of Meynert are classified in basal ganglia, and ammon's horn to cingulate gyrus are classified in limbic system. In this manner, the cortex region has a hierarchical structure of classifications of the kind of a gyrus.

FIG. 5 is a diagram illustrating a generalized example of the hierarchical structure of cortex regions. In FIG. 5, "g1" to "g20" each represent the kind of a gyrus. "Sub-region1" represents a small category of gyri, and "region1", "region2", and "region3" each represent a middle category of gyri. "right hemisphere" and "left hemisphere" each represent a large category of gyri, where "right hemisphere" represents the right hemisphere of a brain and "left hemisphere" represents the left hemisphere of the brain.

Although FIG. 5 illustrates the example of categorizing gyri in a cortex region into a hierarchical structure, gyri are present not only in a cortex region but also in a white matter region as described above. Thus, for example, gyri in both of a cortex region and a white matter region may be categorized into a hierarchical structure. In this case, gyri in the cortex region and the white matter region are classified based on, for example, a hierarchical structure defined by Talairach et al. (1988). The hierarchical structure of Talairach has five levels of hemisphere, lobe, gyrus, tissue, and cell type. Among these, the level of hemisphere is the largest category, and the levels of lobe, gyrus, tissue, cell type, and sub-cell type are smaller categories in this order.

FIG. 6 is a diagram illustrating a generalized example of the hierarchical structure of cortex regions and white matter regions. For example, as illustrated in FIG. 6, the hierarchical structure of gyri included in a cortex region and a white matter region each include the sub-cell type level (sub-cell type) obtained by further segmentalizing the cell type, in addition to the five levels of the hemisphere level, the lobe level, the gyrus level, the tissue level, and the cell type level.

In FIG. 6, "hemisphere1" represents a category included in the hemisphere level. "lobe1" and "lobe2" represent categories included in the lobe level. "gyrus1", "gyrus2", and "gyrus3" represent categories included in the gyrus level. "gray matter" and "white matter" represent categories included in the tissue level. "cell type1" and "cell type2" represent categories included in the cell type level. "g1" to "g14" each represent the kind of a gyrus. As illustrated in FIG. 6, the kinds of a gyrus represented by "g1" to "g14" do not necessarily need to be in the same level.

The category "gray matter" included in the tissue level represents a cortex (gray matter) region, and "white matter" represents a white matter region. In other words, the hierarchical structure illustrated in FIG. 6 includes both of the cortex region (gray matter) and the white matter region (white matter).

Although the above describes the example in which gyri are classified into the hierarchical structure defined by Talairach equal to al. (1988), the embodiment is not limited thereto. For example, gyri may be classified based on various kinds of brain atlases defined by various kinds of companies or various kinds of organizations. The generalized hierarchical structure as described above can be changed as appropriate through segmentalization or consolidation depending on definitions of gyrus categories in various kinds of brain atlases.

In the present embodiment, the memory circuitry 11 stores therein information on separate matrices for cortex regions and white matter regions as a disordered region to be diagnosed by functionally dividing fiber-clusters connecting the brain functional localized regions described above and connecting the brain functional localized region and an organ system.

Specifically, the memory circuitry 11 stores therein information on a matrix representing connectivity between a cortex region and a white matter region for each of the above-described three kinds of fiber-clusters. In other words, the memory circuitry 11 stores therein a matrix representing connectivity through association fibers, a matrix representing connectivity through commissural fibers, and a matrix representing connectivity through projection fibers.

In the following, the matrix representing the connectivity through association fibers is referred to as an association fiber matrix (AFM). The matrix representing the connectivity through commissural fibers is referred to as a commissural fiber matrix (CFM). The matrix representing the connectivity through projection fibers is referred to as a projection fiber matrix (PFM).

Figure 7:
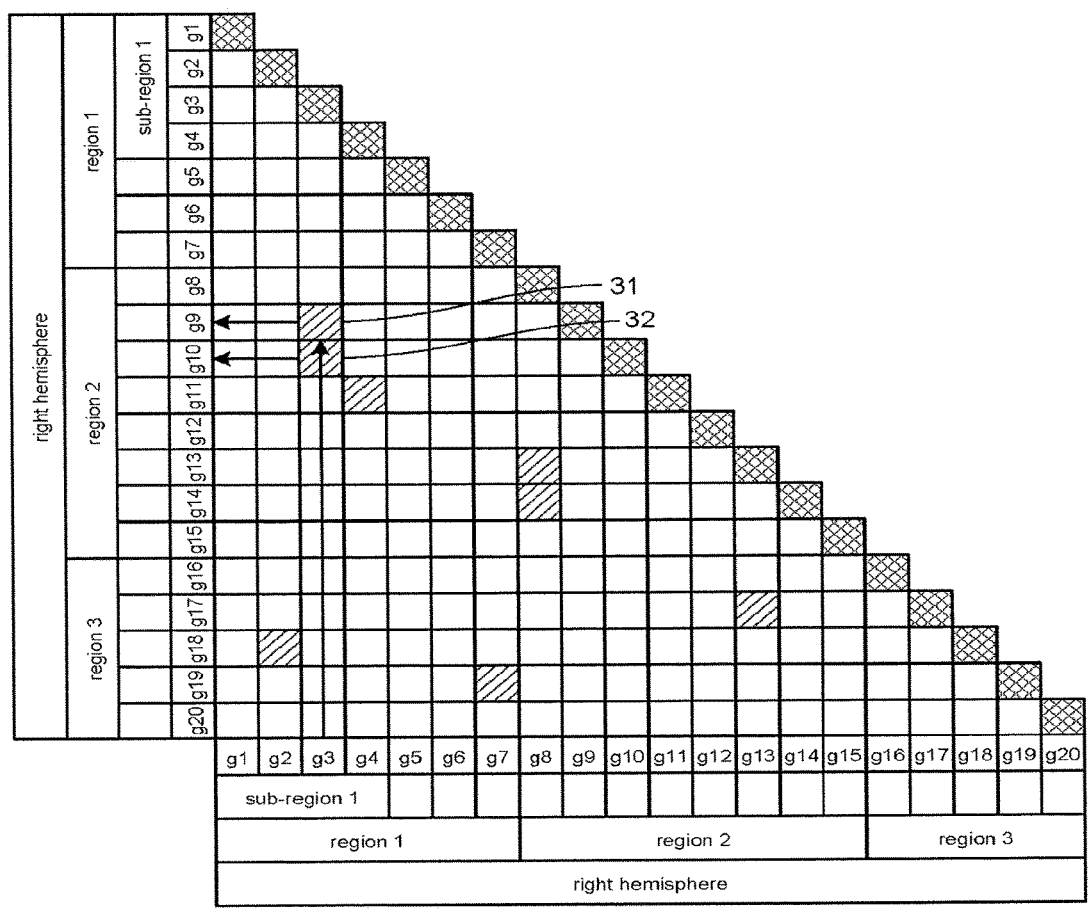
FIG. 7 is a diagram illustrating an exemplary AFM according to the first embodiment.
Figure 8:
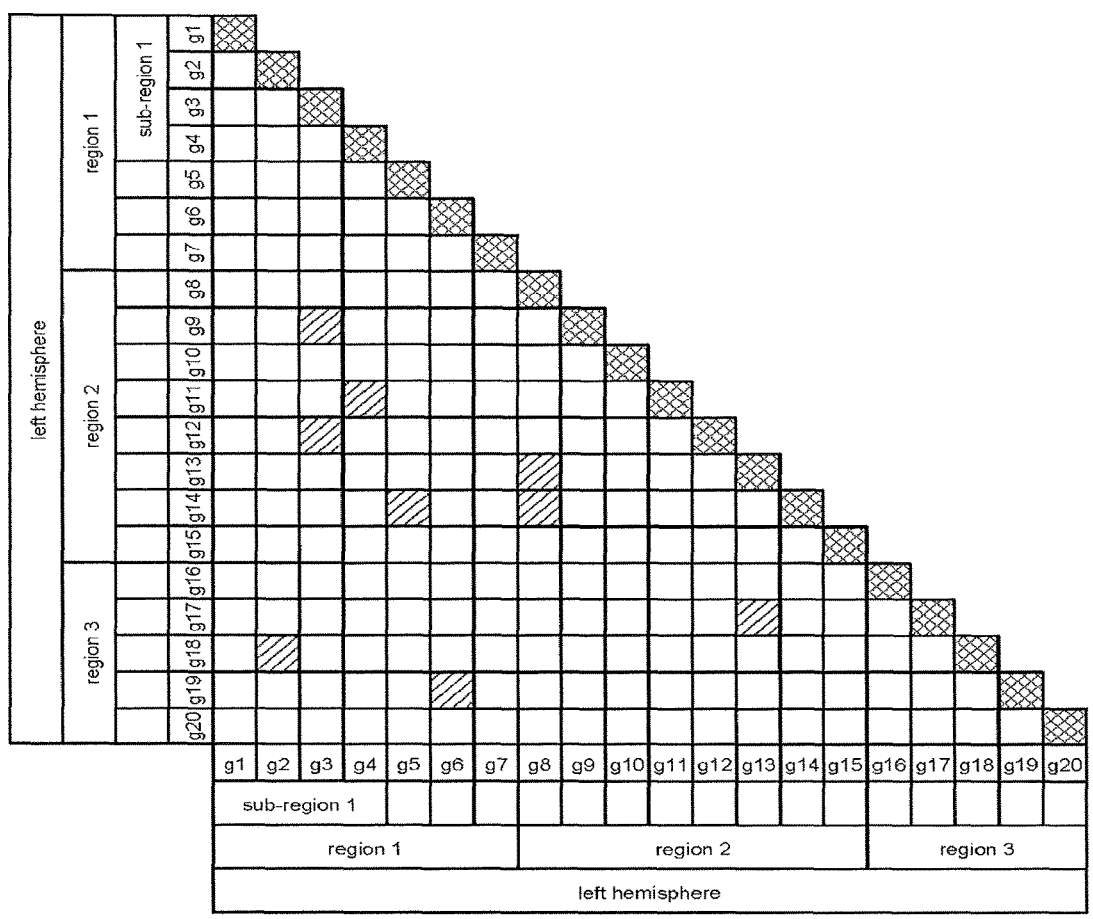
FIG. 8 is a diagram illustrating another exemplary AFM according to the first embodiment.

FIGS. 7 and 8 are each a diagram illustrating an exemplary AFM according to the first embodiment. As described above, an association fiber connects cortex regions included in the same hemisphere of a brain. Thus, the AFM is classified into an AFM related to the right hemisphere or an AFM related to the left hemisphere. FIG. 7 illustrates an example of the AFM related to the right hemisphere, and FIG. 8 illustrates an example of the AFM related to the left hemisphere. These AFMs have the same configuration, and thus the following describes the AFM related to the right hemisphere as an example.

For example, as illustrated in FIG. 7, the AFM is a matrix in which cells "g1" to "g20" each representing a gyrus as the minimum unit of a cortex region are arranged along the horizontal axis and the vertical axis, and cells each representing a white matter region containing a fiber-cluster connecting a gyrus on the horizontal axis and a gyrus on the vertical axis are two-dimensionally arranged along the horizontal and vertical axes. In the AFM, cells representing classifications of the kind of a gyrus having a hierarchical structure are arranged outside the cells representing gyri along the horizontal and vertical axes.

In the AFM illustrated in FIG. 7, a hatched cell represents a white matter region containing a fiber-cluster connecting a gyrus at a corresponding position on the horizontal axis and a gyrus at a corresponding position on the vertical axis. For example, in the information on the AFM, "1" is provided to a cell representing a white matter region containing a fiber-cluster connecting gyri at corresponding positions, and "0" is provided to a cell representing a white matter region containing a fiber-cluster not connecting gyri at corresponding positions. In FIG. 7, a cross-hatched cell corresponds to identical gyri allocated on the horizontal and vertical axes, and is a void cell representing no connectivity.

For example, a cell 31 illustrated in FIG. 7 represents a white matter region containing a fiber-cluster connecting a gyrus represented by cell "g3" arranged on the horizontal axis and a gyrus represented by cell "g9" arranged on the vertical axis. In other words, the cell 31 represents connectivity between the gyrus represented by cell "g3" arranged on the horizontal axis and the gyrus represented by cell "g9" arranged on the vertical axis. Similarly, a cell 32 illustrated in FIG. 7 represents a white matter region containing a fiber-cluster connecting the gyrus represented by cell "g3" arranged on the horizontal axis and a gyrus represented by cell "g10" arranged on the vertical axis. In other words, the cell 32 represents connectivity between the gyrus represented by cell "g3" arranged on the horizontal axis and the gyrus represented by "g10" arranged on the vertical axis. In other words, in the example illustrated in FIG. 7, the gyrus represented by cell "g3" arranged on the horizontal axis is connected with both of the gyrus represented by cell "g9" arranged on the vertical axis and the gyrus represented by cell "g10".

With such an AFM, for example, a search with a search start position at any one of cells "g1" to "g20" arranged along the horizontal axis allows for detection of a white matter region and a gyrus having connectivity with a gyrus represented by a cell at the search start position. In other words, with the AFM, a search with a search start position at one of a plurality of gyrus cells allows for detection of a gyrus having connectivity among other gyri included in the same hemisphere, and a white matter region containing a fiber-cluster connecting these gyri.

Figure 9:
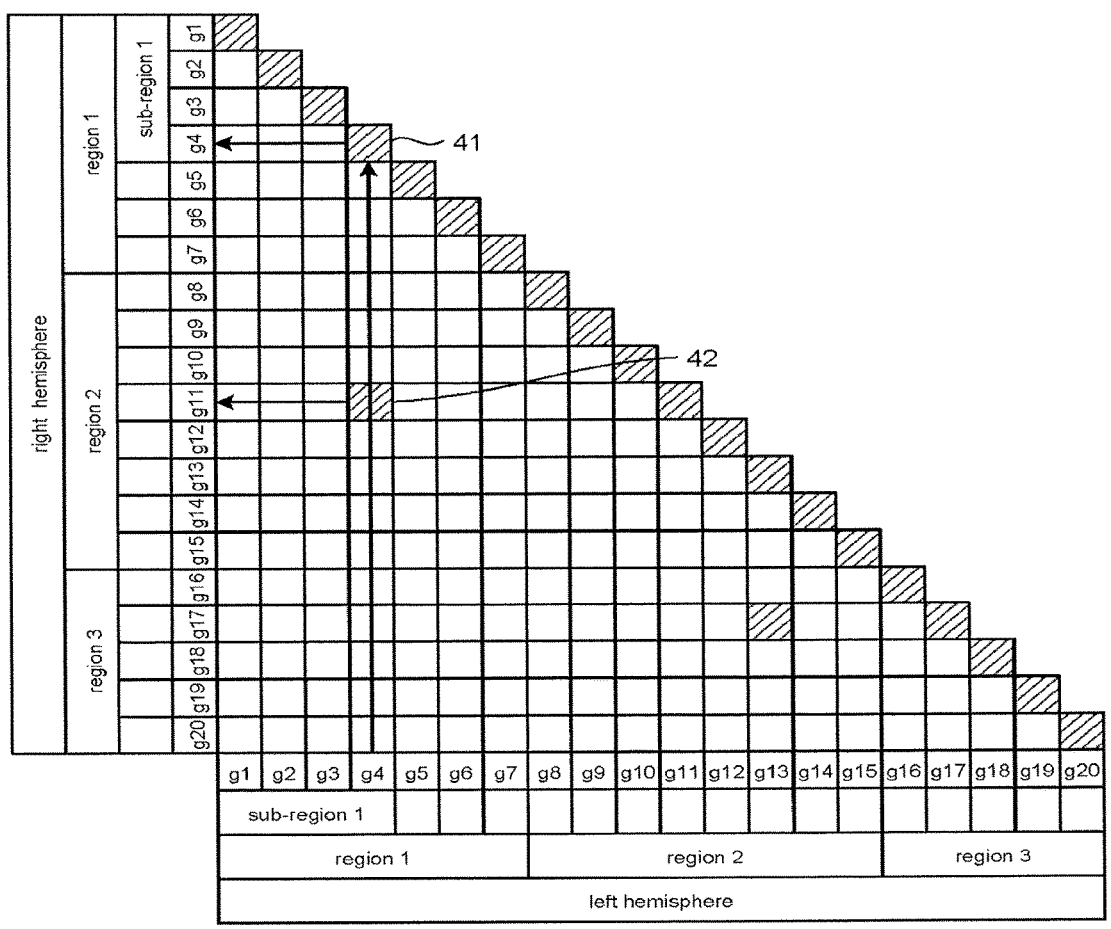
FIG. 9 is a diagram illustrating an exemplary CFM according to the first embodiment.

FIG. 9 is a diagram illustrating an exemplary CFM according to the first embodiment. As described above, a commissural fiber connects a cortex region included in the left hemisphere of a brain and a cortex region included in the right hemisphere. Thus, in the CFM, for example, gyri included in the left hemisphere are allocated on the horizontal axis, and gyri included in the right hemisphere are allocated on the vertical axis.

For example, as illustrated in FIG. 9, the CFM is a matrix in which cells "g1" to "g20" representing gyri included in the left hemisphere are arranged along the horizontal axis, cells "g1" to "g20" representing gyri included in the right hemisphere are arranged on the vertical axis, and cells each representing a white matter region containing a fiber-cluster connecting a gyrus on the horizontal axis and a gyrus on the vertical axis are two-dimensionally arranged along the horizontal and vertical axes. In the CFM, cells representing classifications of the kind of a gyrus having a hierarchical structure are arranged outside the cells representing gyri along the horizontal and vertical axes.

In the CFM illustrated in FIG. 9, similarly to cells included in the AFM described above, a hatched cell represents a white matter region containing a fiber-cluster connecting a gyrus at a corresponding position on the horizontal axis and a gyrus at a corresponding position on the vertical axis. For example, in the information on the CFM, "1" is provided to a cell representing a white matter region containing a fiber-cluster connecting gyri at corresponding positions, and "0" is provided to a cell representing a white matter region containing a fiber-cluster not connecting gyri at corresponding positions.

In the AFM illustrated in FIGS. 7 and 8, a cell corresponding to identical gyri allocated on the horizontal and vertical axes is a void cell representing no connectivity. In contrast, in the CFM illustrated in FIG. 9, the vertical axis and the horizontal axis correspond to the left and right hemispheres, respectively, and thus a cell at the same position as that of a void cell in the AFM represents connectivity between gyri of the same kind included in the left and right hemispheres.

For example, a cell 41 illustrated in FIG. 9 represents a white matter region containing a fiber-cluster connecting a gyrus in the left hemisphere represented by cell "g4" arranged on the horizontal axis and a gyrus in the right hemisphere represented by cell "g4" arranged on the vertical axis. In other words, the cell 41 represents connectivity between the gyrus in the left hemisphere represented by cell "g4" arranged on the horizontal axis and the gyrus in the right hemisphere represented by cell "g4" arranged on the vertical axis. Similarly, a cell 42 illustrated in FIG. 9 represents a white matter region containing a fiber-cluster connecting the gyrus in the left hemisphere represented by cell "g4" arranged on the horizontal axis and a gyrus in the right hemisphere represented by cell "g11" arranged on the vertical axis. In other words, the cell 42 represents connectivity between the gyrus in the left hemisphere represented by cell "g4" arranged on the horizontal axis and the gyrus in the right hemisphere represented by cell "g11" arranged on the vertical axis. In other words, in the example illustrated in FIG. 9, the gyrus in the left hemisphere represented by cell "g4" arranged on the horizontal axis is connected with both of the gyrus in the right hemisphere represented by cell "g4" arranged on the vertical axis and the gyrus in the right hemisphere represented by cell "g11".

With such a CFM, similarly to the AFM, for example, a search with a search start position at any one of cells "g1" to "g20" arranged along the horizontal axis allows for detection of a white matter region and a gyrus having connectivity with the gyrus represented by the cell at the search start position. In other words, with the CFM, a search with a search start position at a cell representing a gyrus included in one of the right and left hemispheres allows for detection of a gyrus having connectivity among gyri included in the other hemisphere, and a white matter region containing a fiber-cluster connecting these gyri.

Figure 10:
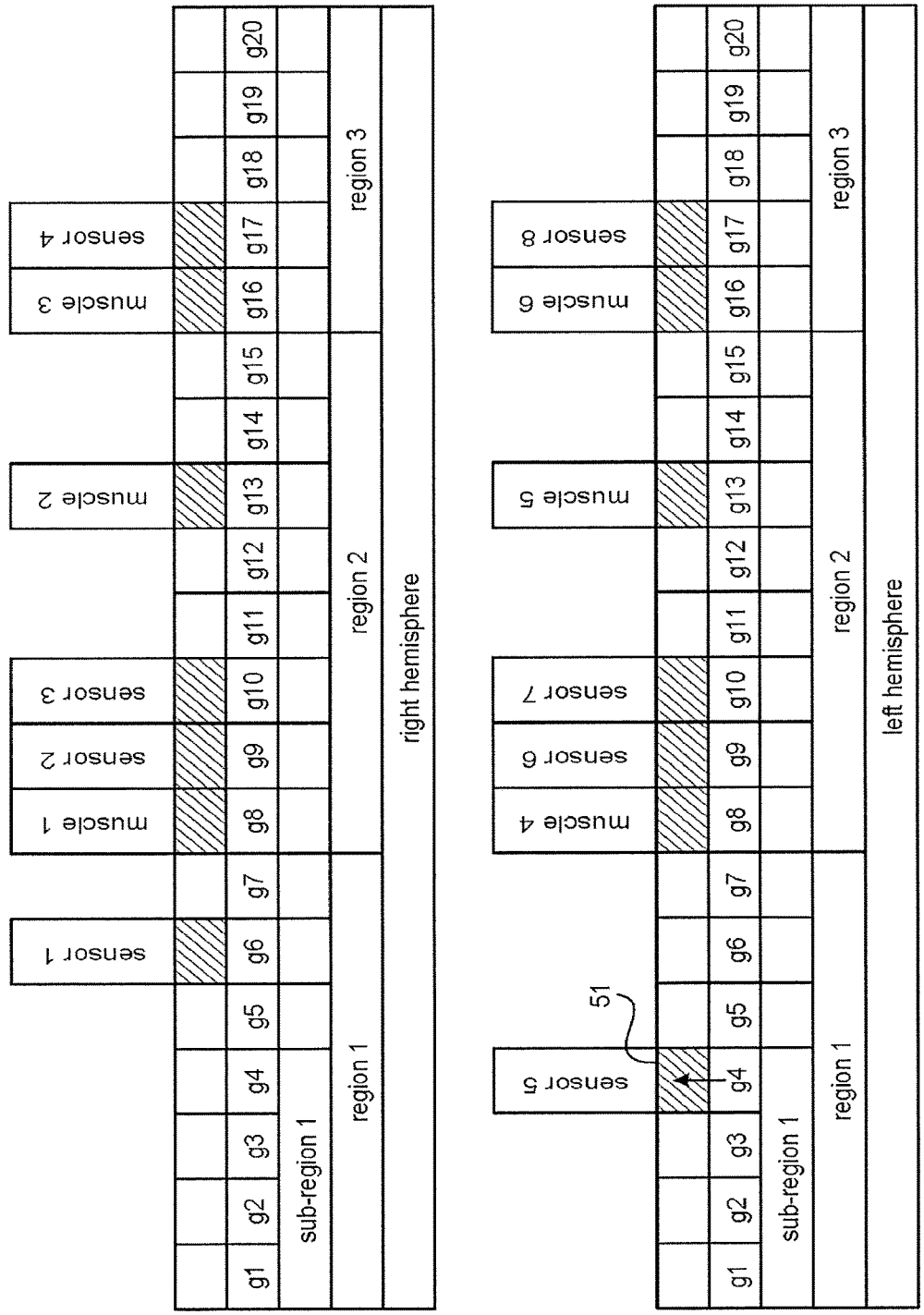
FIG. 10 is a diagram illustrating an exemplary PFM according to the first embodiment.

FIG. 10 is a diagram illustrating an exemplary PFM according to the first embodiment. As described above, a projection fiber connects a cortex region and a white matter region. Thus, the PFM is classified into a PFM related to the right hemisphere or a PFM related to the left hemisphere. The upper diagram in FIG. 10 illustrates an example of the PFM related to the right hemisphere, and the lower diagram of FIG. 10 illustrates an example of the PFM related to the left hemisphere. These PFMs have the same configuration, and thus the following describes the PFM related to the left hemisphere as an example.

For example, as illustrated in FIG. 10, the PFM is a matrix in which cells "g1" to "g20" each representing a gyrus as the minimum unit of a cortex region are arranged along the horizontal axis, and cells each representing a white matter region containing a fiber-cluster connecting a gyrus on the horizontal axis and an organ system are arranged along the horizontal axis. The organ system is, for example, a locomotor apparatus system or a sensory apparatus system. In other words, the PFM corresponds to a list of an organ system connected with each gyrus. A typical clinical symptom is a disorder of any of these organs, and thus this PFM directly represents the clinical symptom. In the PFM, cells representing classifications of the kind of a gyrus having a hierarchical structure are arranged below the cells representing gyri.

As described above, a projection fiber is classified into an efferent projection fiber from a cortex region toward a white matter region or an afferent projection fiber from a white matter region to a cortex region. Thus, a cell representing a white matter region containing a fiber-cluster connecting a gyrus on the horizontal axis and an organ system is provided with information indicating whether the fiber-cluster is efferent or afferent.

As described above, a projection fiber is a nerve fiber coupling a brain functional localized region and a sensory apparatus (input) or a locomotor apparatus (output). Thus, a cell representing a white matter region containing a fiber-cluster connecting a gyrus on the horizontal axis and an organ system is also provided with information indicating the kind of the organ system to which the fiber-cluster is connected.

In the PFM illustrated in FIG. 10, a hatched cell represents a white matter region containing a fiber-cluster connecting a gyrus at a corresponding position on the horizontal axis and an organ system. For example, in the information on the PFM, "+1" is provided to a cell representing a white matter region containing a fiber-cluster connecting a gyrus at a corresponding position and an organ system when the fiber-cluster is efferent, and "−1" is provided to the cell when the fiber-cluster is afferent. For example, in the information on the PFM, "0" is provided to a cell representing a white matter region containing a fiber-cluster not connecting a gyrus at a corresponding position and an organ system. In addition, a label indicating the kind of the organ system is provided to a cell representing a white matter region connecting a gyrus at a corresponding position and an organ system.

For example, a cell 51 illustrated in FIG. 10 represents a white matter region containing a fiber-cluster connecting a gyrus represented by cell "g4" arranged on the horizontal axis and an organ system. In other words, the cell 51 represents connectivity between the gyrus represented by cell "g4" arranged on the horizontal axis and the organ system.

For example, "sensor1" to "sensor8" illustrated in FIG. 10 each represent the kind of a sensory apparatus, and "muscle1" to "muscle6" each represent the kind of a locomotor apparatus. The kind of a sensory apparatus is, for example, eye, ear, nose, tang, or skin. The kind of a locomotor apparatus is, for example, muscle of a hand, muscle of a leg, or facial muscle. In the example illustrated in FIG. 10, in the PFM related to the right hemisphere, a gyrus corresponding to cell "g6" is connected with a sensory apparatus represented by "sensor1", and a gyrus corresponding to cell "g8" is connected with a locomotor apparatus represented by "muscle1". In the example illustrated in FIG. 10, in the PFM related to the left hemisphere, a gyrus corresponding to cell "g4" is connected with a sensory apparatus represented by "sensor5", and the gyrus corresponding to cell "g8" is connected with a locomotor apparatus represented by "muscle4".

With such a PFM, for example, a search with a search start position at any one of cells "g1" to "g20" arranged along the horizontal axis allows for detection of a white matter region and an organ system having connectivity with a gyrus represented by the cell at the search start position. In other words, with the PFM, a search with a search start position at one of a plurality of gyrus cells allows for detection of an organ system having connectivity with the gyrus, and a white matter region containing a fiber-cluster connecting the gyrus and the organ system. In addition, whether a fiber-cluster contained in the detected white matter region is efferent or afferent can be detected.

In the present embodiment, the memory circuitry 11 stores therein information on a matrix in which an attention degree in accordance with a diagnosis purpose and a disease is set to each of a plurality of brain functional localized regions. In the following, such a matrix is referred to as a disease specific attention matrix (DSAM).

Specifically, the memory circuitry 11 stores therein information on the DSAM for each diagnosis purpose. The diagnosis purpose includes definitive diagnosis and screening. In other words, the memory circuitry 11 stores therein information on the DSAM for definitive diagnosis and information on the DSAM for screening.

The memory circuitry 11 stores therein information on the DSAM for definitive diagnosis for each disease. Examples of the disease include Alzheimer's disease and Parkinson's disease. The memory circuitry 11 stores therein information on the DSAM for screening not for a specific disease. In other words, the screening needs to be performed not for a specific disease, and thus a DSAM integrating a plurality of diseases is set for the screening. In this manner, the memory circuitry 11 stores therein information on the DSAM of which content is different between the definitive diagnosis and the screening.

FIG. 11 is a diagram illustrating an exemplary DSAM according to the first embodiment. For example, as illustrated in FIG. 11, the DSAM is a matrix in which cells "g1" to "g20" each representing a gyrus as the minimum unit of a cortex region, cells "f1" to "f8" each representing a fiber-cluster are arranged along the horizontal axis, and cells each representing an attention degree of each gyrus or fiber-cluster on the horizontal axis are arranged above the gyrus or the fiber-cluster. In the DSAM, cells representing classifications of the kind of a gyrus having a hierarchical structure are arranged outside the cells representing gyri.

For example, a predilection degree is set as the attention degree for each brain functional localized region as a predilection site of a disease. Specifically, in the DSAM for definitive diagnosis, a predilection degree of a brain functional localized region as a predilection site of each disease is set as the attention degree. For example, rank values "0" to "4" depending on a P value obtained from past literature information are set as the attention degree, as described below. In this example, a larger rank value indicates a higher predilection degree. In other words, each rank value indicates the likelihood of a predilection site as an abnormality candidate region.

Rank value "0": No attention needed
Rank value "1": $0.050 \leq P$ value<0.100: As a reference
Rank value "2": $0.010 \leq P$ value<0.050
Rank value "3": $0.001 \leq P$ value<0.010
Rank value "4": $0.000 \leq P$ value<0.001

For example, $-\log(P)$ may be used as the attention degree. For $P=10^{-4}$ as an example, $-\log(10^{-4})=4$ is set as the attention degree.

In the DSAM for screening, the same attention degree is set to all cells each representing a gyrus or a fiber-cluster. For example, in the DSAM for screening, rank value "3" as the attention degree is set to all cells each representing a gyrus or a fiber-cluster. In the DSAM for screening, the attention degree may be weighted for each cell representing a gyrus or a fiber-cluster.

The DSAM is not limited to the configuration illustrated in FIG. 11. For example, the DSAM may be configured in a similar manner to the AFM.

Figure 12:
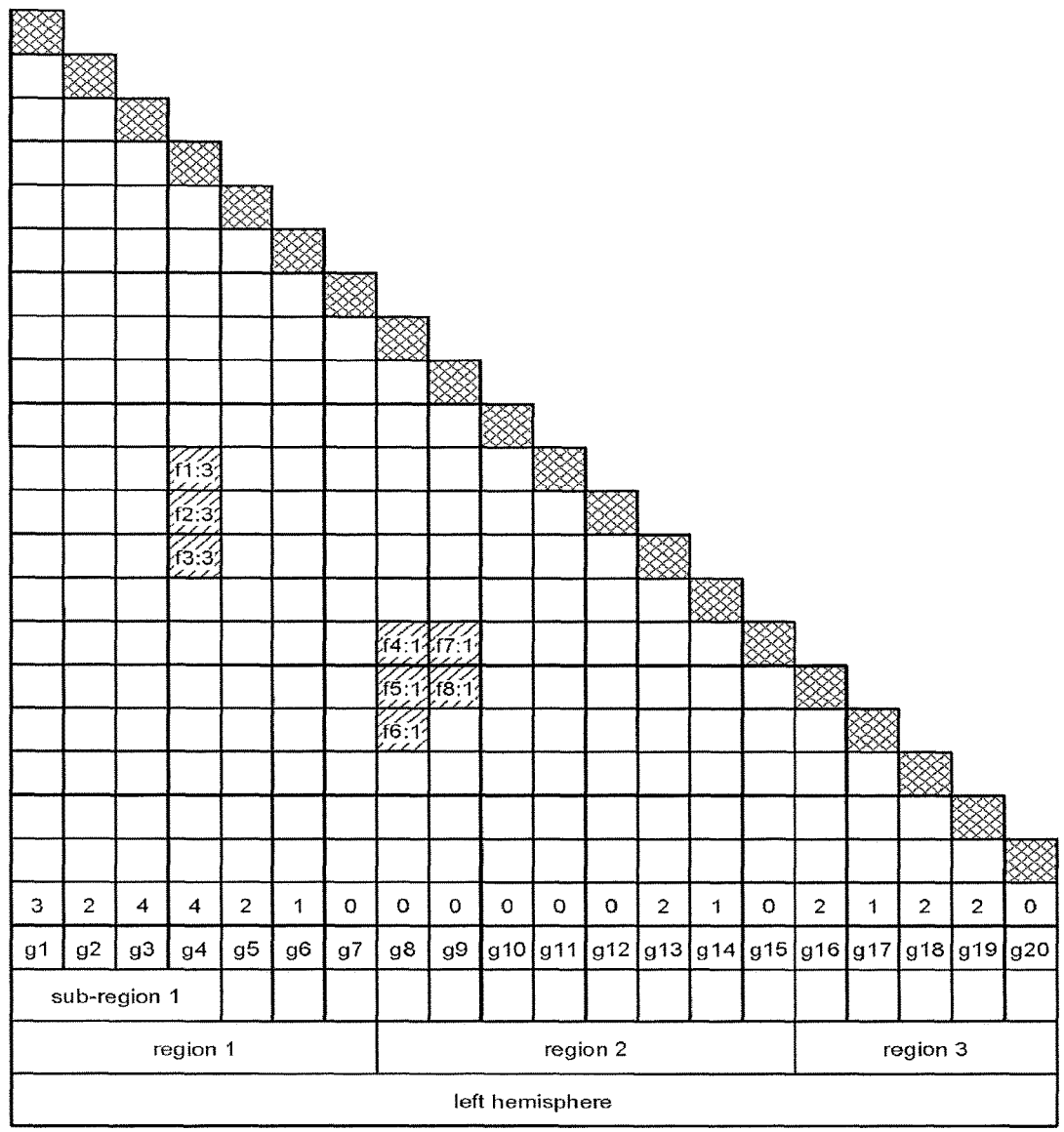
FIG. 12 is a diagram illustrating another exemplary DSAM according to the first embodiment.

FIG. 12 is a diagram illustrating another exemplary DSAM according to the first embodiment. The example illustrated in FIG. 12 illustrates a DSAM related to the left hemisphere, and cells arranged along the vertical axis are not illustrated. For example, as illustrated in FIG. 12, the DSAM may be configured in a similar manner to the AFM. In this case, for example, as illustrated in FIG. 12, one of "f1" to "f8" each indicating a fiber-cluster and the attention degree of the fiber-cluster are set to a cell (hatched cell) representing a white matter region containing a fiber-cluster connecting a gyrus at a corresponding position on the horizontal axis and a gyrus at a corresponding position on the vertical axis.

The above describes the AFM, the CFM, the PFM, and the DSAM stored in the memory circuitry 11. Contents set to each matrix are set based on, for example, previously known literature and experimental results. The contents set to each matrix are updated with information obtained through progress of research and analysis on a clinical case in the field of brain science, based on accumulated images of the subject periodically or at an optional timing. This achieves an improved accuracy.

In the AFM, the CFM, the PFM, and the DSAM, the number of gyri arranged on the horizontal and vertical axes is not limited to the numbers of gyri illustrated in FIGS. 7 to 12, and may be changed as appropriate depending on definitions of categories of brain functional localized regions.

Values set to the AFM, the CFM, the PFM, and the DSAM are not necessarily limited to those described above. For example, in the AFM, the CFM, and the PFM, a value provided to a cell of a white matter region may be a stepped value between "0" to "1". In such a case, a value set to a cell is determined depending on, for example, an analysis value obtained as an analysis result of an image.

For example, the attention degree set to the DSAM may be set based on other reference values than the P value. In other words, the attention degree set to the DSAM may be set based on any other statistical value indicating the likelihood of a predilection site as an abnormality candidate region.

In the present embodiment, image analysis and diagnose determination are proceeded by the processing circuitry 15 dividing an MR image of the subject into brain functional localized regions, analyzing an image of each region, referring to this analysis value and the DSAM to determine the priority of a region that requires attention, and specifying any relevant cortex and white matter in the AFM, the CFM, and the PFM.

As illustrated in FIG. 1, in the present embodiment, the processing circuitry 15 has a setting function 15a, an analyzing function 15b, a specifying function 15c, a searching function 15d, and a display controlling function 15e. The processing circuitry 15 is an exemplary processing circuitry in the claims.

The setting function 15a receives a diagnosis purpose and a diagnose target disease from the operator. Specifically, the setting function 15a receives, from the operator through the input circuitry 9, an operation to specify a diagnosis purpose and a diagnose target disease. In this process, the setting function 15a receives, as the diagnosis purpose, an operation to specify one of the definitive diagnosis and the screening. The setting function 15a also receives an operation to specify a diagnose target disease when the diagnosis purpose is the definitive diagnosis.

When a diagnosis purpose and a disease are specified by the operator, the setting function 15a sets an imaging condition to collect analysis target images, which is determined in advance depending on the diagnosis purpose and the disease. The setting function 15a generates sequence execution data for collecting analysis target images based on the set imaging condition, and transmits the generated sequence execution data to the processing circuitry 13. Consequently, the executing function 13a of the processing circuitry 13 collects MR signal data for generating analysis target images. The image generating function 14a of the processing circuitry 14 generates the analysis target images based on the collected MR signal data.

Examples of the analysis target images include a morphological image such as a T1 Weighted image, a T2 Weighted image, a T2*Weighted image and a fluid attenuation inversion recovery (FLAIR) image, and a functional image such as a susceptibility weighted image, a quantitative susceptibility map (QSM), a diffusion weighted image, a diffusion tensor imaging (DTI) image, a resting state functional MRI (rs-fMRI) image and a diffusion tensor tractography (DTT) image.

For example, the memory circuitry 11 stores therein one or a plurality of protocols to collect images to be used in an analysis, in advance for each kind of a diagnosis purpose and a diagnosis target. Each protocol is information that defines, for example, the kind of a pulse sequence used to collect data for generating images to be collected, and values of various kinds of imaging parameters used to collect this data. When a diagnosis purpose and a disease are specified by the operator, the setting function 15a acquires one or a plurality of protocols corresponding to the specified diagnosis purpose and disease by referring to the memory circuitry 11, and generates sequence execution data to collect images used in an analysis based on the acquired protocol. In this manner, an imaging condition to collect images used in an analysis can be automatically set depending on a diagnosis purpose and a disease.

The images used in analysis includes, in addition to the above-described analysis target images, a morphological image and functional image used by the analyzing function 15b to be described later to perform processing of dividing a brain region included in an analysis target image into a plurality of brain functional localized regions. Examples of the morphological image include a magnetization prepared rapid gradient echo (MP-RAGE) image of the whole brain, and examples of the functional image include a Q-ball imaging (QBI) image of the whole brain. The images used in an analysis also include an image displayed as a reference image by the display controlling function 15e to be described later. Examples of the image displayed as a reference image include a T2 weighted image of the whole brain.

The analyzing function 15b divides a brain region included in an image of the subject into a plurality of brain functional localized regions, and performs a texture analysis on each localized region. For example, the analyzing function 15b performs the texture analysis in terms of parameters such as the intensity value of a pixel, a fractional anisotropy (FA) value in a DTI image, a mean diffusivity (MD) value, an apparent diffusion coefficient (ADC) value, and susceptibility in a quantitative susceptibility map. The texture analysis is, for example, a basic statistical analysis on the average and dispersion of the intensity value in its first order, and analysis on inhomogeneity and the degree of a particular pattern in its second order. Targets of the texture analysis are, for example, an MP-RAGE image, a T2 weighted image, an FA image, and a QSM. In MBs search with a QSM, analysis for voxel-based automatic detection in a region is performed. The analyzing function 15b analyzes a difference in a predetermined parameter from a normal brain for each localized region.

In the above-described process, the analyzing function 15b may perform the texture analysis on a plurality of kinds of parameters for each brain functional localized region. The analyzing function 15b may perform volume calculation for each brain functional localized region. The analyzing function 15b may analyze differences in a plurality of kinds of parameters from the normal brain for each brain functional localized region.

Specifically, when an analysis target image is generated by the image generating function 14a of the processing circuitry 14, the analyzing function 15b analyzes the generated image.

The analyzing function 15b first divides a brain region included in the analysis target image into a plurality of brain functional localized regions. Specifically, for example, the analyzing function 15b performs segmentation into brain functional localized regions by using a morphological image acquired as an analysis image. For example, the analyzing function 15b performs segmentation of a brain region visualized in the morphological image into a plurality of regions by deforming and positioning, in accordance with the morphological image, a model in which a typical brain is divided into a plurality of brain functional localized regions. The morphological image thus used is, for example, a T1 weighted image. Then, the analyzing function 15b applies the brain functional localized regions segmented on the morphological image to another analysis target image so as to divide a brain region included in this image into a plurality of brain functional localized regions.

Then, the analyzing function 15b performs the texture analysis for each gyrus as the minimum unit of a cortex region, and sets an attention degree to the gyrus based on this analysis result. Specifically, similarly to the DSAM, the attention degree is set to rank values "0" to "4" depending on the P value.

In addition, the analyzing function 15b analyzes a difference in the predetermined parameter from the normal brain for each gyrus as the minimum unit of a cortex region, and sets an attention degree to the gyrus based on this analysis result. Specifically, similarly to the DSAM, the attention degree is set to rank values "0" to "4" depending on the P value.

The specifying function 15c specifies a search start position in a matrix representing inter-regional connectivity between a plurality of regions in a brain based on an analysis result on an image of the subject and an attention degree set to each of the regions in the brain.

For example, the specifying function 15c specifies a search start position in a matrix representing inter-regional connectivity between a plurality of brain functional localized regions based on an analysis result on an image of the subject and an attention degree set to each brain functional localized region. Specifically, the specifying function 15c specifies search start positions in the AFM, the CFM, and the PFM using the DSAM in which an attention degree is set to each brain functional localized region in accordance with a diagnosis purpose and a disease.

Specifically, if a diagnosis purpose received by the setting function 15a is the definitive diagnosis, the specifying function 15c uses information on the DSAM corresponding to a disease specified by the operator among information on the DSAM for the definitive diagnosis stored in the memory circuitry 11. If a diagnosis purpose received by the setting function 15a is the screening, the specifying function 15c uses information on the DSAM for the screening stored in the memory circuitry 11.

The specifying function 15c also specifies a search start position using an analysis result of the texture analysis performed by the analyzing function 15b. The specifying function 15c also specifies a search start position using an analysis result of analyzing a difference in the predetermined parameter from the normal brain performed by the analyzing function 15b. A cell specified as a search start position by the specifying function 15c indicates a gyrus or a fiber-cluster as a lesion candidate.

Figure 13:
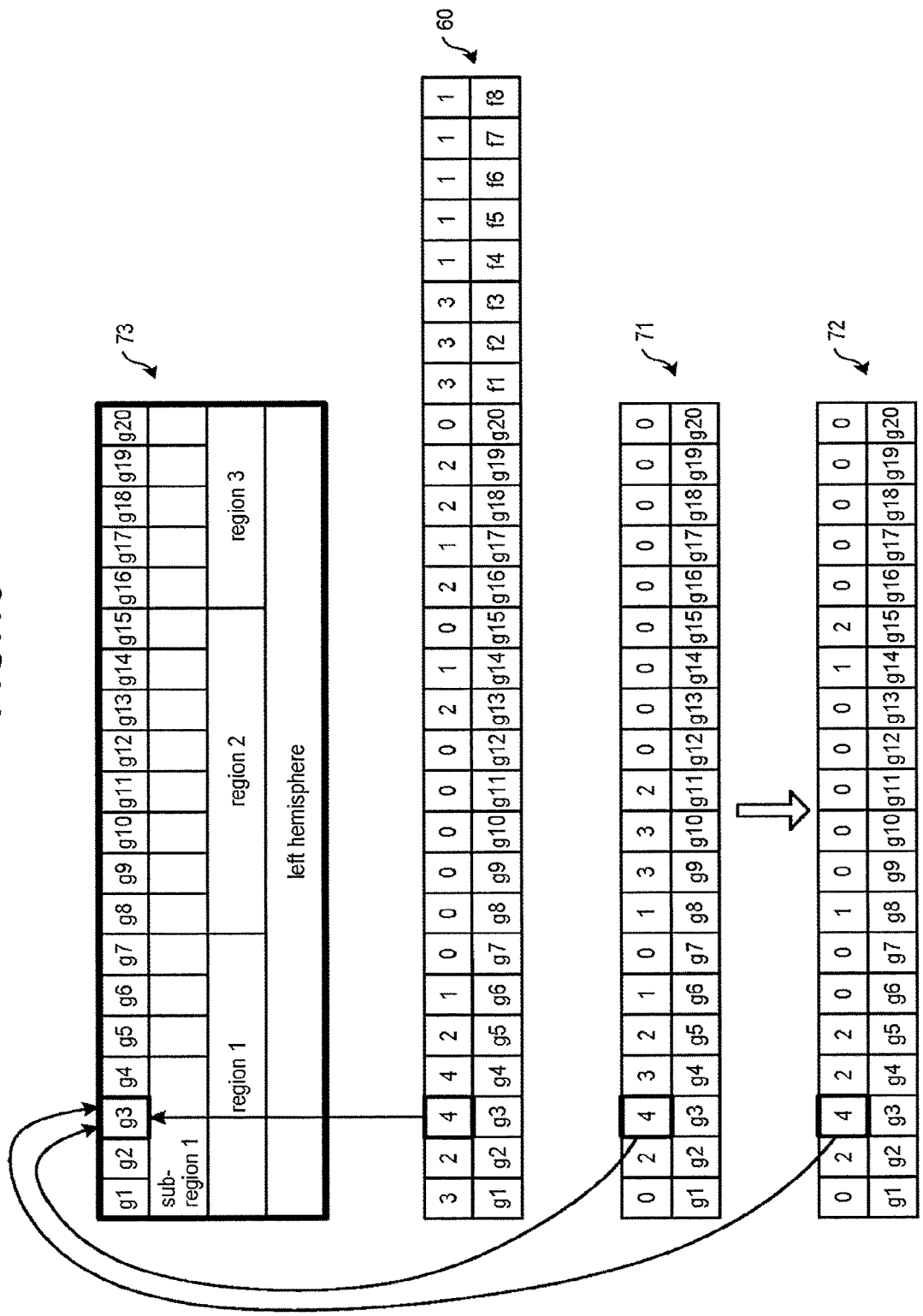
FIG. 13 is a diagram illustrating an example of specification of a search start position by a specifying function according to the first embodiment.

FIG. 13 is a diagram illustrating an example of specification of a search start position by the specifying function 15c according to the first embodiment. For example, as illustrated in FIG. 13, the specifying function 15c specifies a cell of a gyrus and a cell of a fiber-cluster as a search start position from among a plurality of cells "g1" to "g20" and "f1" to "f8" based on a DSAM 60, an analysis result 71 of the texture analysis, and an analysis result 72 on a difference from the normal brain. In FIG. 13, only cells of gyri and attention degrees are illustrated for the DSAM 60. FIG. 13 illustrates an example in which a gyrus represented by cell "g3" is selected as a search start position from among a plurality of gyri 73 represented by cells "g1" to "g20".

For example, the specifying function 15c specifies, as a search start position, a cell having an attention degree equal to or larger than "2" in at least one of the DSAM 60, the analysis result 71, and the analysis result 72. For example, in the example illustrated in FIG. 13, cells "g1" to "g5", "g9" to "g11", "g13", "g15", "g16", "g18", and "g19" and cells "f1" to "f3" are specified as search start positions. When the same attention degree is set to all cells each representing a gyrus or a fiber-cluster in the DSAM for the screening, all of the cells are specified as search start positions.

In the description above, the specifying function 15c specifies, as a search start position, a cell having an attention degree equal to or larger than "2" representing a gyrus or a fiber-cluster, but the attention degree is not limited to this threshold. For example, the specifying function 15c may specify, as a search start position, a cell of a gyrus or a fiber-cluster having an attention degree larger than "0". The specifying function 15c may change the threshold of the attention degree in accordance with, for example, an instruction from the operator.

Although the above describes the example in which the specifying function 15c specifies, as a search start position, a cell having an attention degree equal to or larger than the threshold in at least one of the DSAM 60, the analysis result 71 of the texture analysis, and the analysis result 72 on a difference from the normal brain, the embodiment is not limited thereto.

For example, the specifying function 15c may calculate, for each gyrus, a statistical value of attention degrees set in the DSAM 60, the analysis result 71, and the analysis result 72, and specify, as a search start position, a cell of which the calculated statistical value is equal to or larger than a predetermined threshold. For example, the specifying function 15c calculates, as the statistical value, an average value, a sum, or a product. Alternatively, for example, the specifying function 15c may calculate, as the statistical value, a weighted sum of attention degrees in the DSAM 60, the analysis result 71, and the analysis result 72 with a predetermined ratio.

Alternatively, for example, instead of specifying a search start position using all of the DSAM 60, the analysis result 71, and the analysis result 72, the specifying function 15c may specify a search start position using any one or two of them. In this case, for example, the specifying function 15c receives, through the input circuitry 9, an operation to select any one or two of the DSAM 60, the analysis result 71 of the texture analysis, and the analysis result 72 on a difference from the normal brain, and specifies a search start position based on an attention degree in this selection by the operator.

Alternatively, for example, instead of specifying a search start position using the DSAM 60, the analysis result 71, and the analysis result 72, the specifying function 15c may specify, as a search start position, a cell corresponding to a gyrus specified by the operator.

Alternatively, for example, the specifying function 15c may specify a search start position based on analysis results on a plurality of kinds of parameters obtained by the texture analysis and the volume calculation and an analysis result on differences in the parameters from the normal brain.

Figure 14:
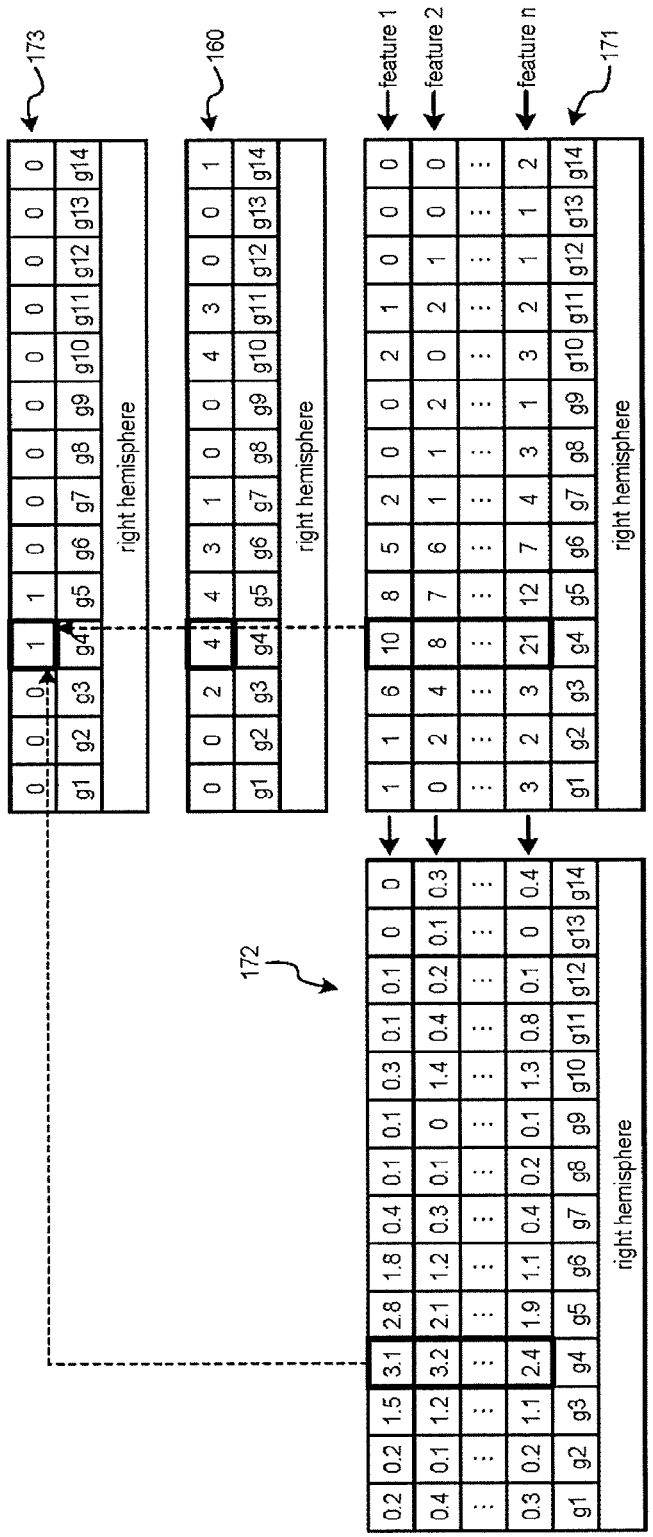
FIG. 14 is a diagram illustrating another example of specification of a search start position by the specifying function according to the first embodiment.

FIG. 14 is a diagram illustrating another example of specification of a search start position by the specifying function 15c according to the first embodiment. For example, as illustrated in FIG. 14, the specifying function 15c specifies a cell of a gyrus and a cell of a fiber-cluster as search start positions from among a plurality of cells "g1" to "g14" based on a DSAM 160, analysis results 171 of the texture analysis and the volume calculation, and an analysis result 172 on a difference from the normal brain. FIG. 14 illustrates the example in which the DSAM 160 includes cells "g1" to "g14" representing gyri. FIG. 14 also illustrates the example in which the analysis results 171 of the texture analysis and the volume calculation and the analysis result 172 on a difference from the normal brain each include analysis results on a plurality of kinds of parameters (feature 1 to feature n).

For example, the specifying function 15c calculates an average value of the attention degree of each gyrus over a plurality of kinds of parameters included in the analysis results 171. Then, the specifying function 15c specifies a cell of a gyrus of which the calculated average value of the attention degree exceeds a predetermined threshold. For example, in the example illustrated in FIG. 13, when the average value of the attention degree of a gyrus of cell "g4" exceeds the threshold, the specifying function 15c specifies cell "g4" as a search start position candidate.

Thereafter, the specifying function 15c determines whether the average value of the attention degree calculated from the analysis results 171 for the cell specified as a search start position candidate is equal to or larger than an attention degree set in the DSAM 160 by referring to the DSAM 160. If the average value of the attention degree calculated from the analysis results 171 is equal to or larger than the attention degree set in the DSAM 160, the specifying function 15c specifies this cell as a search start position. If the average value of the attention degree calculated from the analysis results 171 is smaller than the attention degree set in the DSAM 160, the specifying function 15c excludes this cell as a search start position candidate. For example, in the example illustrated in FIG. 13, if the average value of the attention degree calculated from the analysis results 171 for cell "g4" is equal to or larger than an attention degree of "4" set in the DSAM 160, the specifying function 15c specifies cell "g4" as a search start position.

For example, the specifying function 15c may specify a search start position using the analysis result 172 on a difference from the normal brain in addition to the DSAM 160. In this case, for example, the specifying function 15c calculates the average value of the attention degree of each gyrus over a plurality of kinds of parameters included in the analysis result 172. Then, if the average value of the attention degree calculated from the analysis results 171 for a cell specified as a search start position candidate is equal to or larger than an attention degree set in the DSAM 160 and equal to or larger than the average value of the attention degree calculated from the analysis result 172, the specifying function 15c specifies this cell as a search start position candidate. If the average value of the attention degree calculated from the analysis results 171 is smaller than the attention degree set in the DSAM 160 or smaller than the average value of the attention degree calculated from the analysis result 172, the specifying function 15c excludes this cell as a search start position candidate.

Then, for example, as illustrated in FIG. 13, the specifying function 15c generates a list 173 of a plurality of cells included in the DSAM 160. Then, the specifying function 15c sets label "1" to a cell specified as a search start position in the generated list 173, and label "0" to a cell not specified as a search start position.

The above describes the example in which the specifying function 15c calculates the average value of the attention degree of each gyrus over a plurality of kinds of parameters, but the embodiments are not limited thereto. For example, the specifying function 15c may calculate the sum of the attention degree of each gyrus over the parameters, or may calculate the product thereof. Alternatively, for example, the specifying function 15c may calculate the sum of the attention degree weighted for each parameter by performing a weighted sum of the parameters each weighted at a predetermined ratio. In these cases, the attention degree is set to the DSAM 160 in a similar manner.

As illustrated in FIG. 1, the searching function 15d searches a matrix using a search start position specified by the specifying function 15c. Specifically, the searching function 15d searches each of the AFM, the CFM, and the PFM by referring to information on the AFM, the CFM, and the PFM stored in the memory circuitry 11, and using the cell of a gyrus and the cell of a fiber-cluster specified as search start positions by the specifying function 15c.

FIGS. 15 to 19 are each a diagram illustrating an example of search of a matrix by the specifying function 15c according to the first embodiment. The following describes an example in which cells "g3", "f2", and "f4" are specified as search start positions by the searching function 15d.

Figure 15:
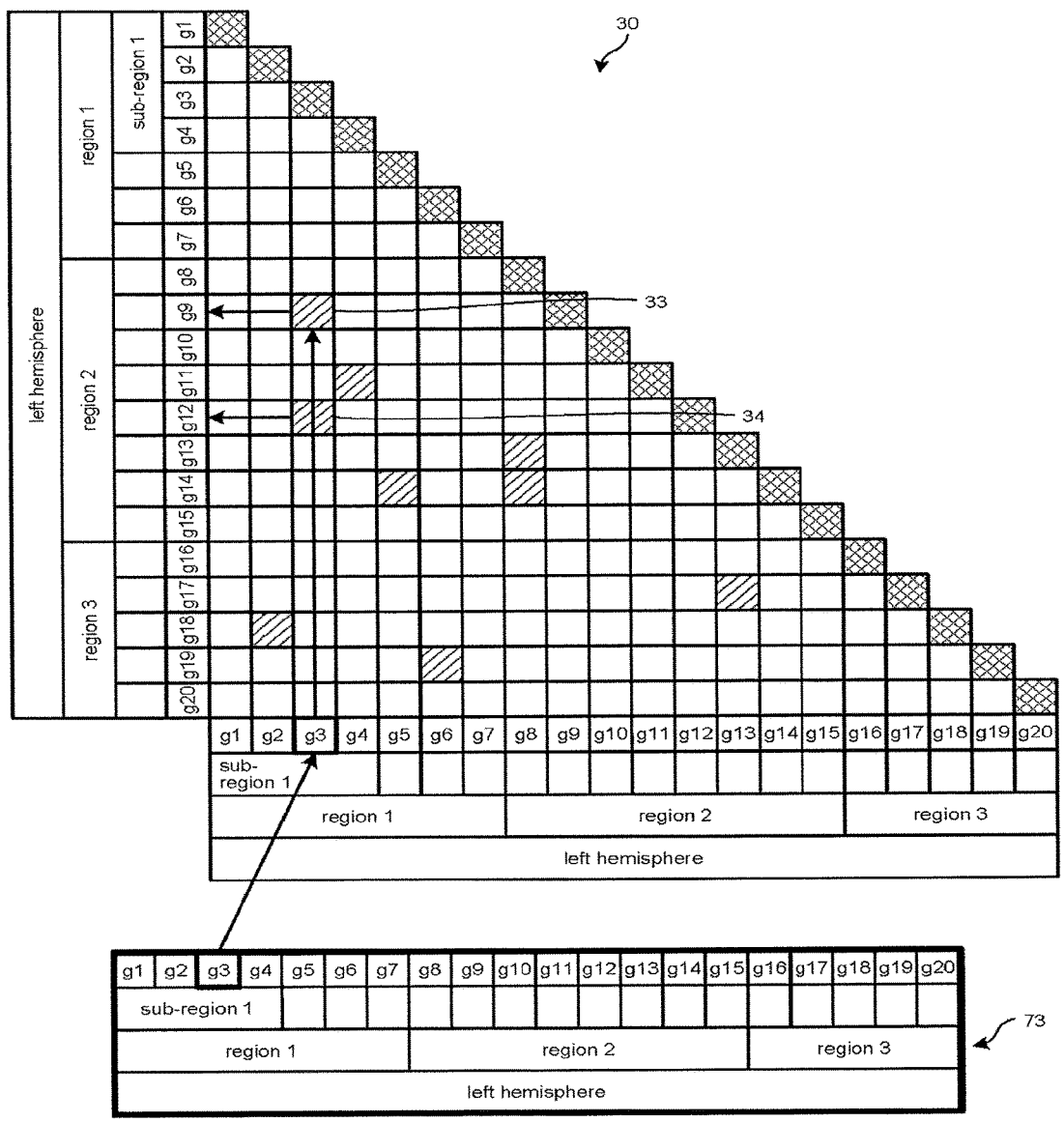
FIG. 15 is a diagram illustrating an example of search of a matrix by the specifying function according to the first embodiment.

For example, as illustrated in FIG. 15, the searching function 15d searches an AFM 30 with a search start position being at cell "g3" specified by the specifying function 15c from among cells "g1" to "g20" arranged along the horizontal axis. In the example illustrated in FIG. 15, this obtains white matter regions represented by cells 33 and 34 and gyri represented by cells "g9" and "g12" as white matter regions and gyri each having connectivity with a gyrus represented by cell "g3" in the same brain hemisphere.

Figure 16:
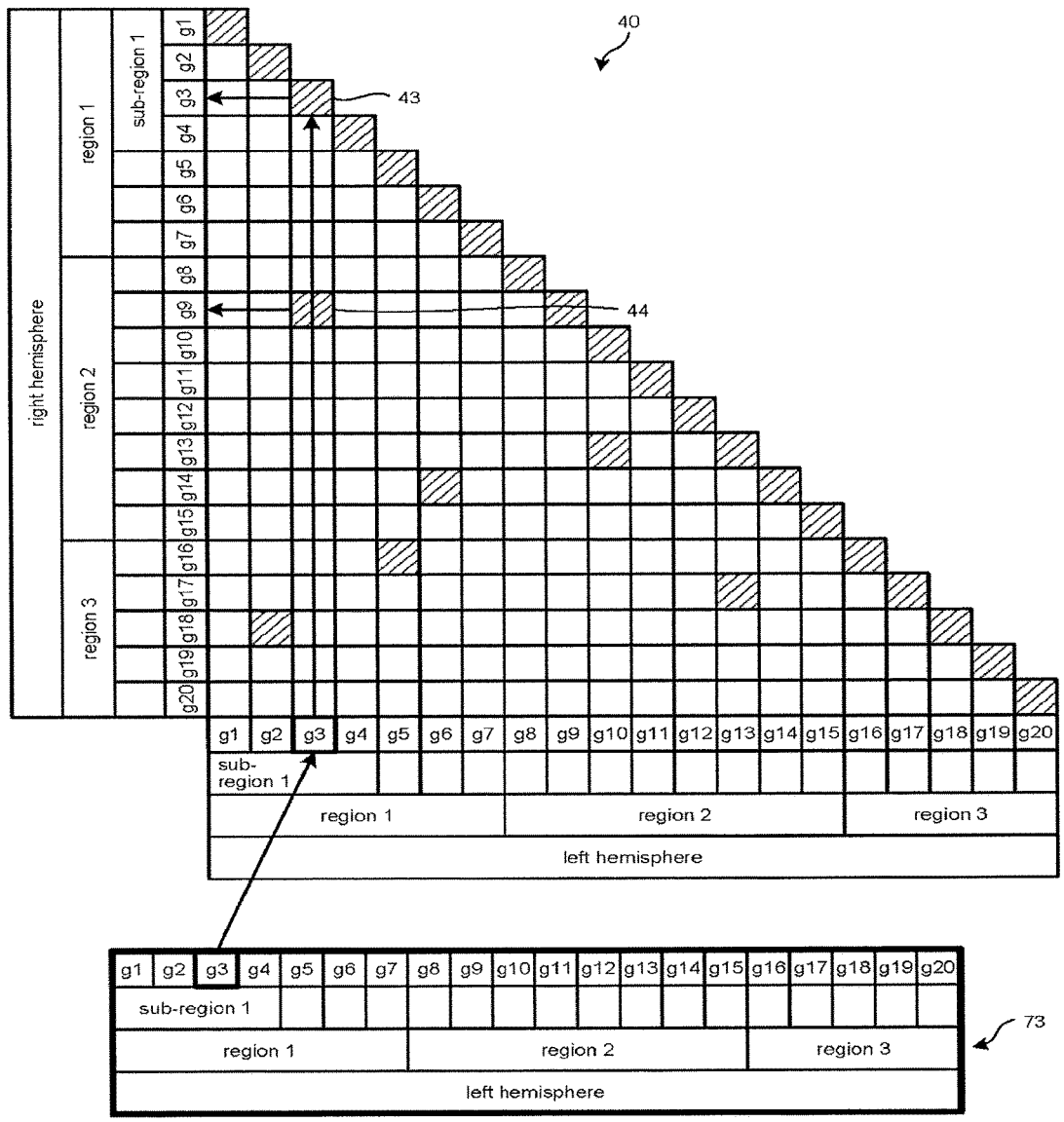
FIG. 16 is a diagram illustrating an example of search of a matrix by the specifying function according to the first embodiment.

For example, as illustrated in FIG. 16, the searching function 15d searches a CFM 40 with a search start position being at cell "g3" specified by the specifying function 15c from among cells "g1" to "g20" arranged along the horizontal axis. In the example illustrated in FIG. 16, this obtains white matter regions represented by cells 43 and 44 and gyri represented by cells "g3" and "g9" as white matter regions and gyri each having connectivity with the gyrus represented by cell "g3" in the opposite brain hemisphere.

Figure 17:
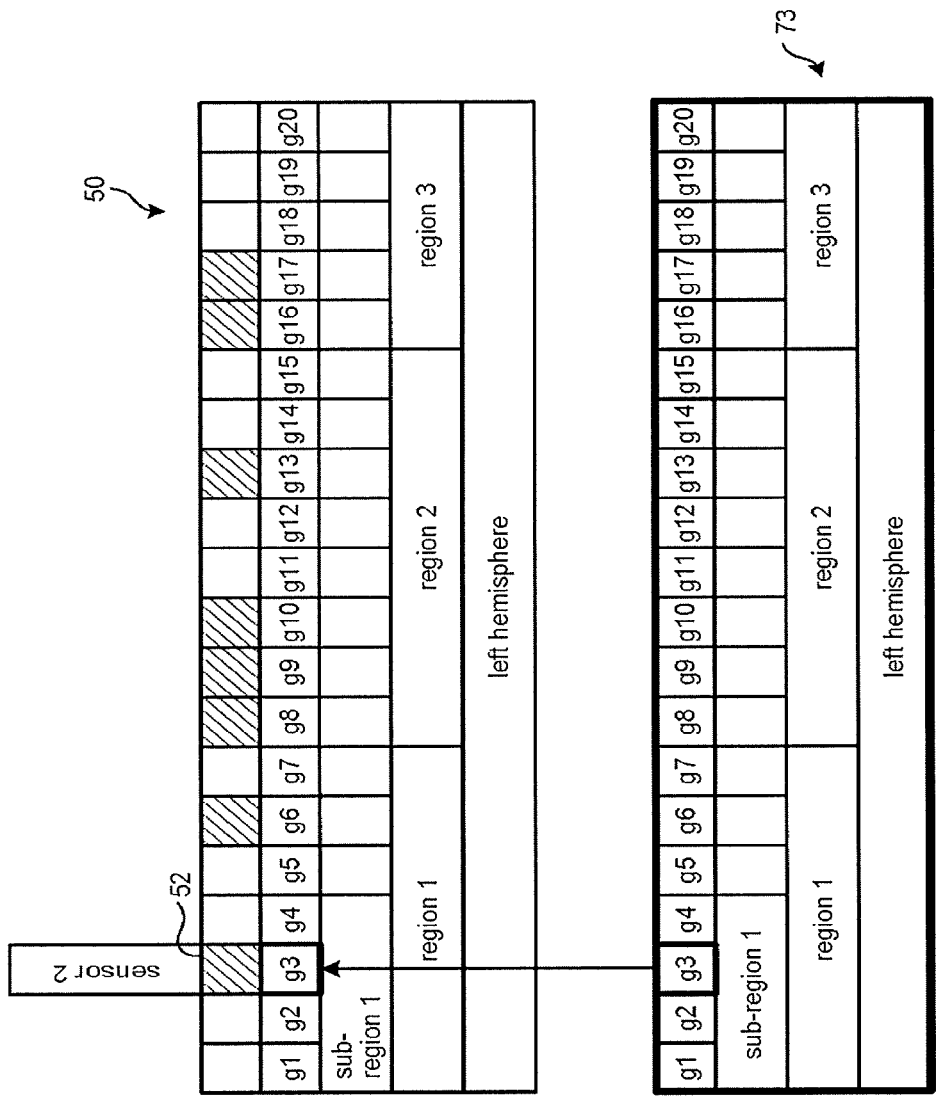
FIG. 17 is a diagram illustrating an example of search of a matrix by the specifying function according to the first embodiment.

For example, as illustrated in FIG. 17, the searching function 15d searches a PFM 50 with a search start position being at cell "g3" specified by the specifying function 15c from among cells "g1" to "g20" arranged along the horizontal axis. In the example illustrated in FIG. 17, this obtains a white matter region represented by a cell 52 and an organ system as a white matter region and an organ system each having connectivity with the gyrus represented by cell "g3". For example, the searching function 15d detects a sensory apparatus represented by "sensor2" as an organ system having connectivity with the gyrus represented by cell "g3". Simultaneously, it is detected by referring to information added to the cell 52 whether a fiber-cluster included in the specified white matter region is efferent or afferent.

Figure 18:
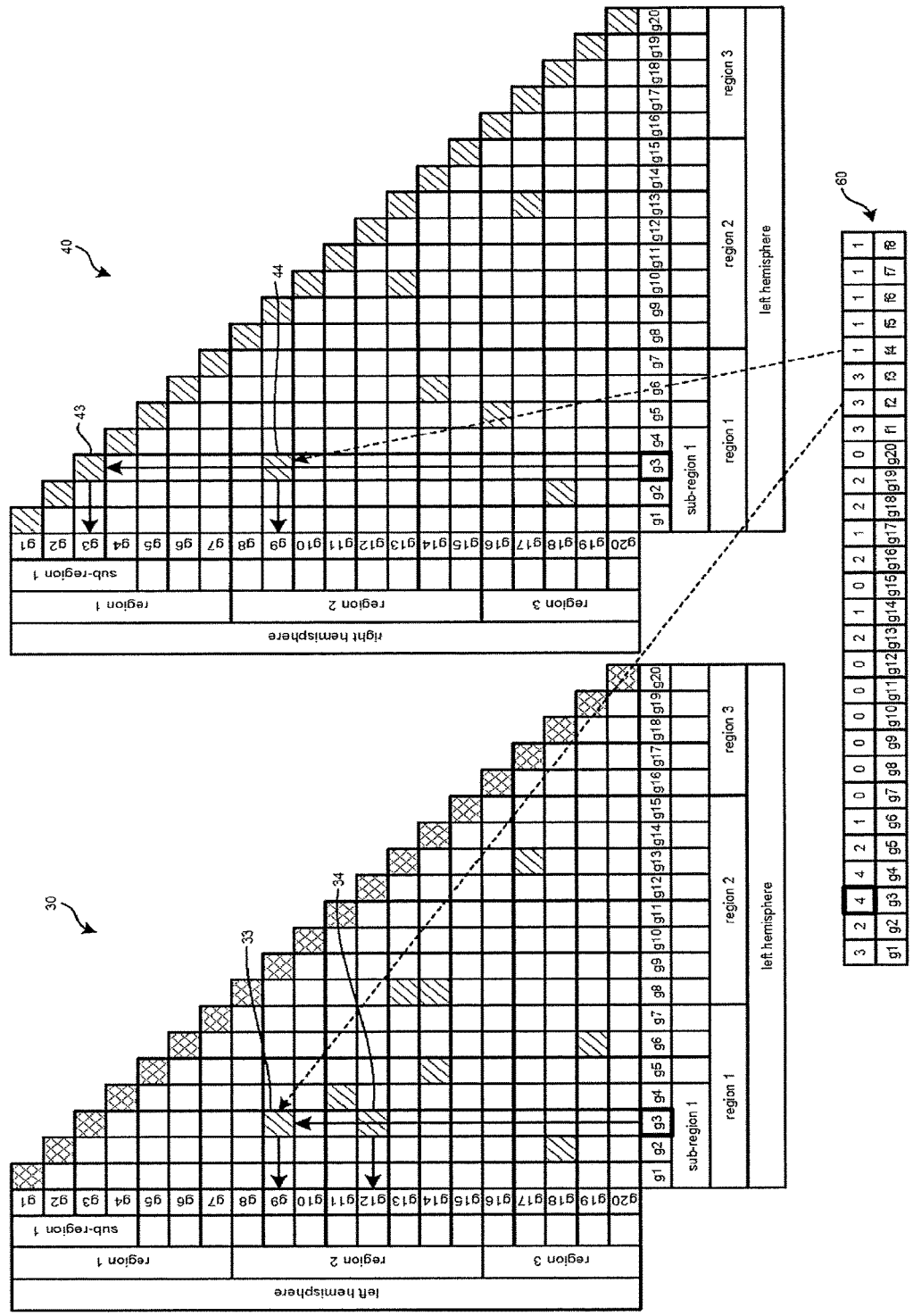
FIG. 18 is a diagram illustrating an example of search of a matrix by the specifying function according to the first embodiment.

For example, as illustrated on a left side in FIG. 18, the searching function 15d searches the AFM 30 with a search start position being at cell "f2" specified by the specifying function 15c from among cells "g1" to "g20" arranged along the horizontal axis. In the example illustrated in FIG. 18, this specifies cell 33 representing a white matter region containing a fiber-cluster represented by cell "f2". As a result, the gyrus represented by cell "g3" arranged on the horizontal axis and the gyrus represented by cell "g9" arranged on the vertical axis are obtained as gyri connected through the fiber-cluster represented by cell "f2" in the same brain hemisphere.

Similarly, for example, as illustrated on a right side in FIG. 18, the searching function 15d searches the CFM 40 with a search start position being at cell "f4" specified by the specifying function 15c from among cells "g1" to "g20" arranged along the horizontal axis. In the example illustrated in FIG. 18, this specifies a cell 44 representing a white matter region containing a fiber-cluster represented by cell "f4". As a result, a gyrus in the left hemisphere represented by cell "g3" arranged on the horizontal axis and a gyrus in the right hemisphere represented by cell "g9" arranged on the vertical axis are obtained as gyri connected through the fiber-cluster represented by cell "f4".

Figure 19:
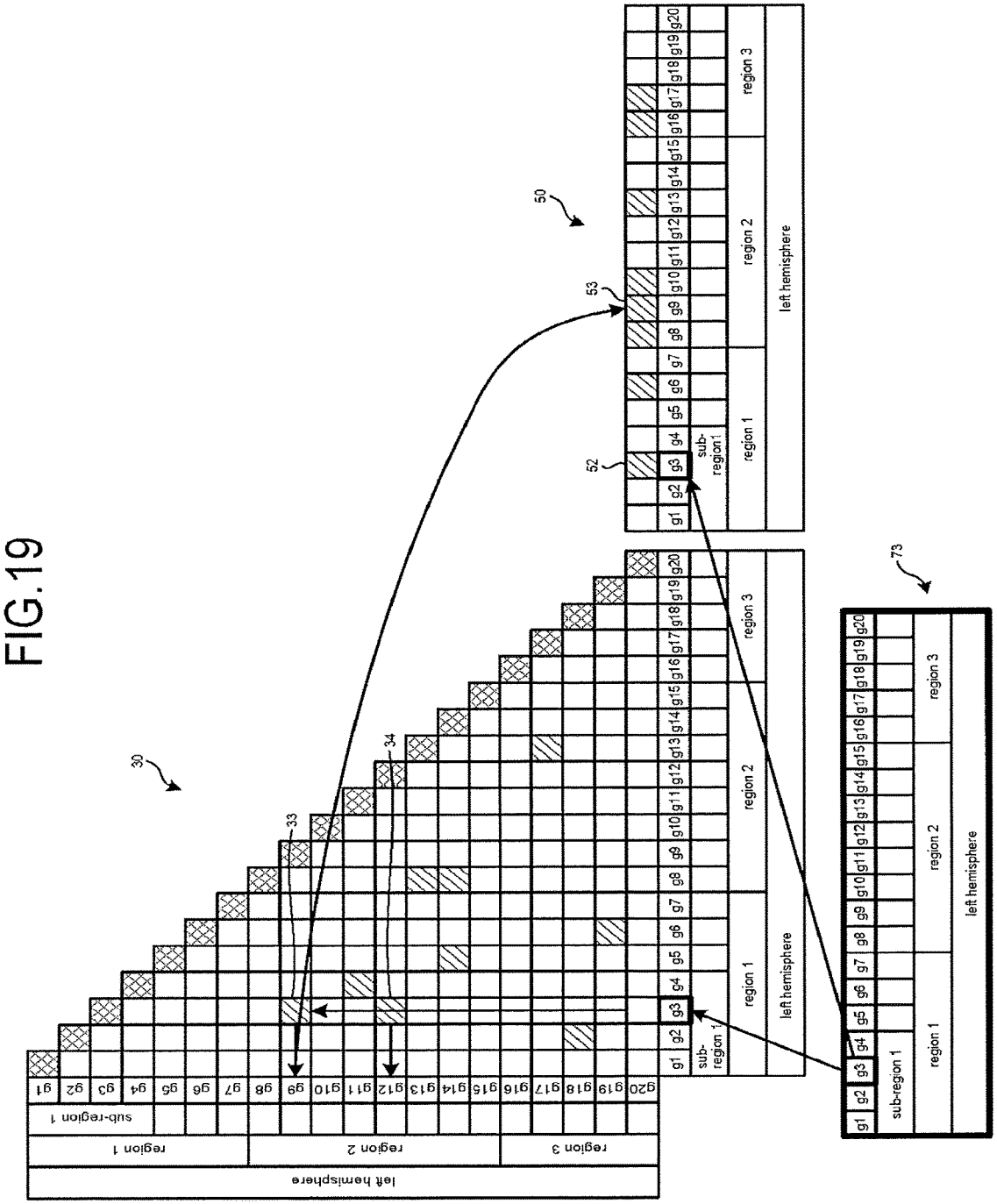
FIG. 19 is a diagram illustrating an example of search of a matrix by the specifying function according to the first embodiment.

The specifying function 15c may further search the matrices using the search results of the matrices. For example, as illustrated in FIG. 19, after the gyrus represented by cell "g9" is obtained as a gyrus having connectivity with a gyrus represented by cell "g3" as a result of the search of the AFM 30 as illustrated in FIG. 15, the searching function 15d further searches the PFM 50 with a search start position being at cell "g9" thus searched. In the example illustrated in FIG. 19, this obtains a white matter region represented by a cell 53 and an organ system as a white matter region and an organ system each having connectivity with the gyrus represented by cell "g9". Simultaneously, it is detected by referring to information added to the cell 53 whether a fiber-cluster included in the specified white matter region is efferent or afferent.

The above describes the example in which cells "g3", "f2", and "f4" are specified as search start positions by the searching function 15d. However, the searching function 15d searches the AFM, the CFM, and the PFM with a search start position being at each of all gyri and fiber-clusters specified by the specifying function 15c.

Such a configuration enables search of a brain functional localized region having a disorder at a gyrus level for a patient having a clinical symptom or a patient candidate having no symptoms but suffering a pathological change.

For example, in order to present a lesion candidate based on a clinical symptom, a "direct search" can be performed to search a brain functional localized region linked with a projection fiber coupled with a sensory apparatus or a locomotor apparatus directly related to the clinical symptom, and an "indirect search" can be performed to search a vulnerable brain functional localized region coupled with a brain functional localized region (epicenter) having a lesion.

For example, as illustrated in FIG. 19, when the gyrus represented by cell "g3" is specified as a lesion candidate by the specifying function 15c, the searching function 15d can specify an organ system connected with the gyrus represented by cell "g3" by searching the PFM 50 with a search start position being at cell "g3". This search of an organ system connected with a gyrus specified as a lesion candidate is referred to as the "direct search".

The search of the AFM 30 by the searching function 15d reveals that the gyrus represented by cell "g3" is connected with the gyrus represented by cell "g9" and the gyrus represented by cell "g12". For example, the search of the PFM 50 by the searching function 15d with a search start position being at cell "g9" can specify an organ system connected with the gyrus represented by cell "g9". This search of an organ system connected with another gyrus connected with a gyrus specified as a lesion candidate is referred to as the "indirect search".

Recent studies have found that, when a gyrus suffers an abnormality, another gyrus having connectivity with this gyrus also suffers an abnormality.

According to the configuration above, the indirect search of the gyrus represented by cell "g3" specifies an organ system connected with the gyrus represented by cell "g9", for example, even when the gyrus represented by cell "g9" is not specified as a lesion candidate because of its low attention degree as in the example illustrated in FIG. 19. Thus, if a clinical symptom is confirmed on the organ system specified by the indirect search of the gyrus represented by cell "g3" for an actual patient, this allows an estimation that the gyrus represented by cell "g9" is affected by the gyrus represented by cell "g3" and suffering an abnormality. This can prevent the abnormality of the gyrus represented by cell "g9" from being missed in diagnosis.

As illustrated in FIG. 1, the display controlling function 15e performs control to display a search result of a matrix by the searching function 15d.

For example, the display controlling function 15e displays a search result of a matrix by the searching function 15d on the display 10.

In the present embodiment, the display controlling function 15e performs control to display, as a search result of a matrix, a matrix representing inter-regional connectivity between a plurality of regions in the brain. Specifically, the display controlling function 15e performs control to selectively display part of a plurality of regions arranged along a first axis of the matrix, based on the attention degree set to each of the region in the brain.

For example, the display controlling function 15e displays, as a search result of a matrix on the display 10, a matrix representing inter-regional connectivity between a plurality of brain functional localized regions. Specifically, the display controlling function 15e selectively displays part of a plurality of brain functional localized regions arranged along the horizontal axis of the matrix, based on the attention degree set to each brain functional localized region.

Specifically, the display controlling function 15e displays, on the display 10, a matrix in which information indicating part of the brain functional localized regions is arranged along the horizontal axis, and information indicating each brain functional localized region having connectivity with each of the brain functional localized regions arranged along the horizontal axis is arranged along the vertical axis.

In the present embodiment, the display controlling function 15e displays a matrix in which a cell specified as a search start position by the specifying function 15c from among a plurality of cells arranged along the horizontal axis in the AFM, the CFM, or the PFM is arranged along the horizontal axis, each cell representing a gyrus or a fiber-cluster. In this case, the display controlling function 15e arranges cells of white matter regions and gyri obtained through the search by the searching function 15d along the vertical axis.

In other words, the display controlling function 15e selectively displays the content of the AFM, the CFM, or the PFM along the horizontal and vertical axes. Although the following describes an example of displaying the AFM, a matrix having selected contents can be displayed in the same procedure for the CFM and the PFM.

Figure 20:
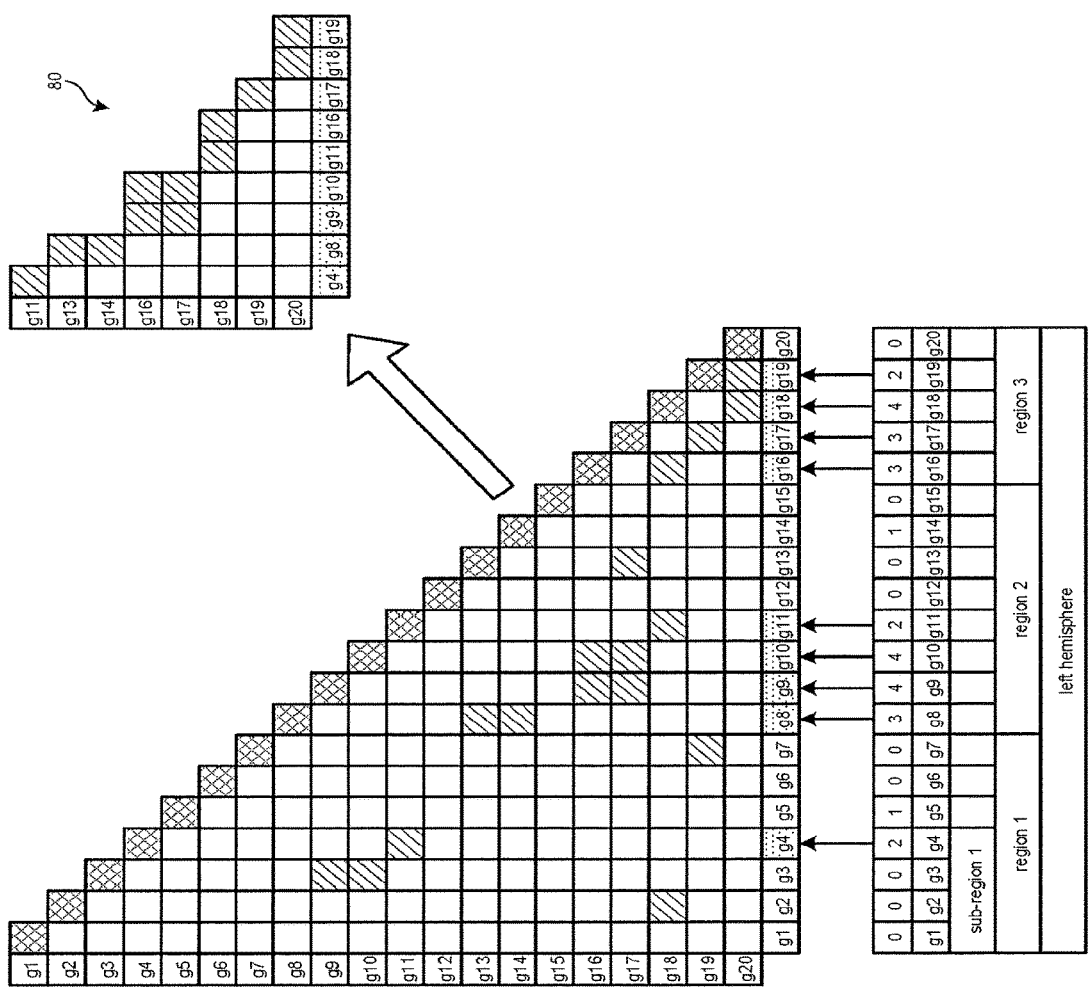
FIG. 20 is a diagram illustrating an example of display of a matrix by a display controlling function according to the first embodiment.

FIG. 20 is a diagram illustrating an example of display of a matrix by the display controlling function 15e according to the first embodiment. In FIG. 20, an exemplary DSAM is illustrated at the lower-left, and an exemplary AFM is illustrated at the upper-left. FIG. 20 illustrates an example in which cells "g4", "g8" to "g11", and "g16" to "g19" are specified as search start positions by the specifying function 15c. FIG. 20 illustrates an example in which cells "g11", "g13", "g14", and "g16" to "g20" along the vertical axis are obtained as search results by the searching function 15d.

In this case, as illustrated at the upper-right in FIG. 20, the display controlling function 15e displays, on the display 10, a matrix 80 in which cells "g4", "g8" to "g11", and "g16" to "g19" are arranged along the horizontal axis, cells "g11", "g13", "g14", and "g16" to "g20" are arranged along the vertical axis, and a cell of a white matter region corresponding to each cell is arranged.

At the same time, the display controlling function 15e hierarchically displays, along the horizontal and vertical axes, information indicating a brain functional localized region, and information indicating a functional or anatomical category to which the brain functional localized region belongs.

Figure 21:
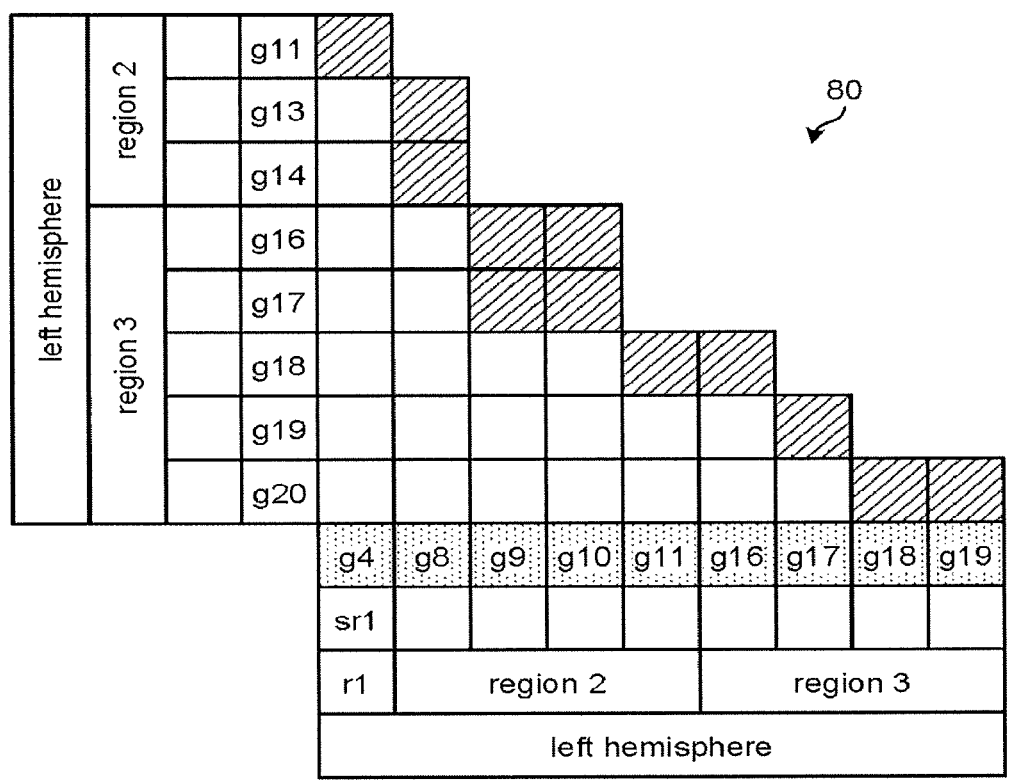
FIG. 21 is a diagram illustrating an example of detailed display of a matrix by the display controlling function according to the first embodiment.

FIG. 21 is a diagram illustrating an example of detailed display of a matrix by the display controlling function 15e according to the first embodiment. For example, as illustrated in FIG. 21, the display controlling function 15e displays cells representing classifications of the kind of a gyrus having a hierarchical structure, outside cells representing gyri along the horizontal and vertical axes. For example, the display controlling function 15e displays cells of "sr1" representing a small category of gyri, cells of "r1", "region2", and "region3" each representing a middle category of gyri, a cell of "left hemisphere" representing a large category of gyri, in this order from the cells representing gyri.

The display controlling function 15e may display abbreviations of the cells having the hierarchical structure, like "r1" and "sr1" illustrated in FIG. 21, for example. Specifically, "r1" is an exemplary abbreviation of "region1", and "sr1" is an exemplary abbreviation of "sub-regioin1". The display controlling function 15e may switch display and non-display of information having a hierarchical structure in accordance with an instruction from the operator.

In addition, in accordance with an operation to select a brain functional localized region displayed on the display 10, the display controlling function 15e displays an image of the selected brain functional localized region on the display 10. In this case, the display controlling function 15e displays a zoomed image of the brain functional localized region on the display 10. The display controlling function 15e also displays, on the display 10, arrangement of an image of some brain functional localized regions arranged along the horizontal axis in the matrix 80, and an image of brain functional localized regions having connectivity with these brain functional localized regions.

In this manner, display of a matrix having selected contents allows easier recognition of a brain functional localized region having a high attention degree. For example, in a case of Alzheimer's disease, display of the AFM for a selection of neural circuits representing a memory function and an emotion function allows easy association of a clinical symptom and a brain functional localized region.

Figure 22:
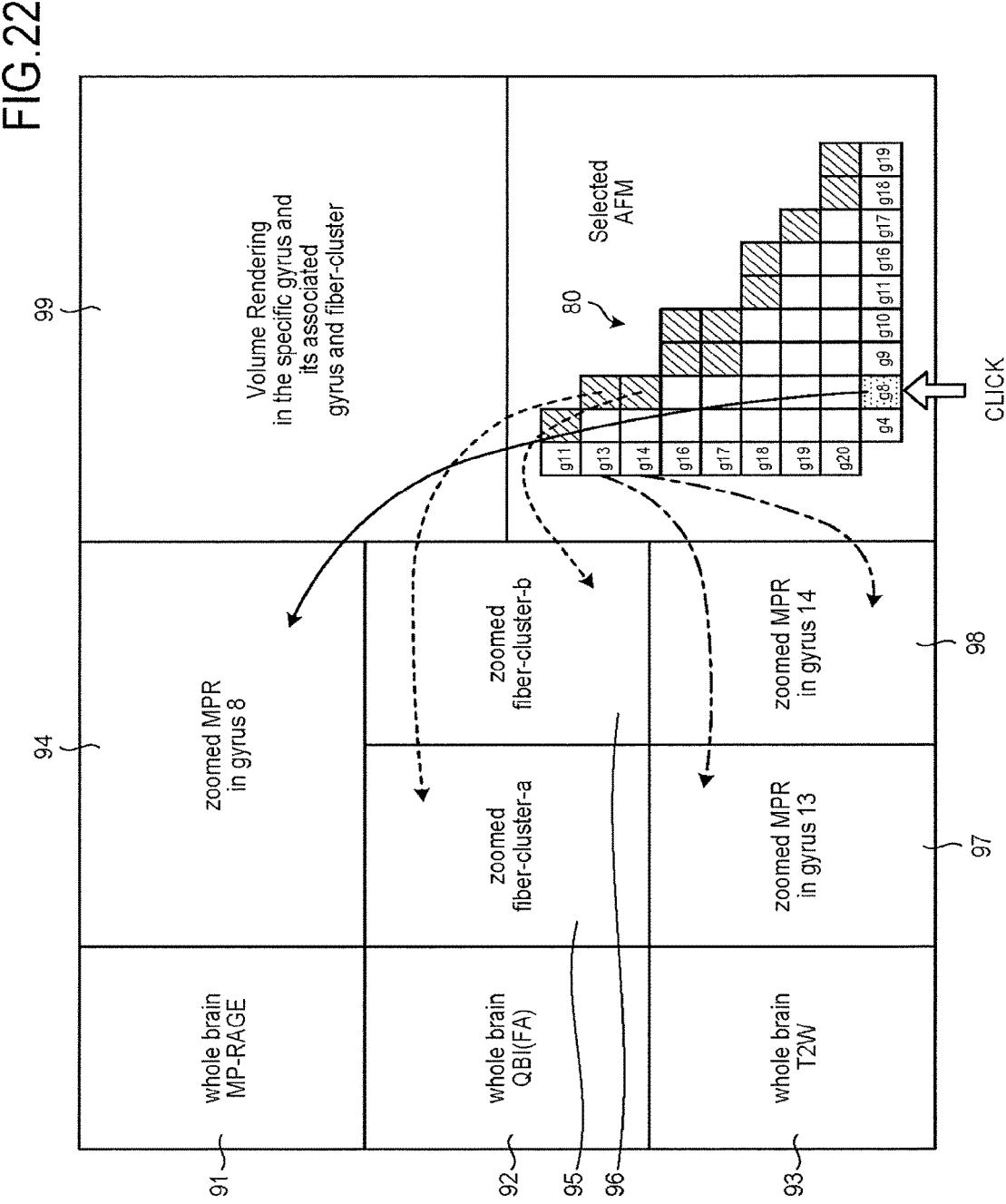
FIG. 22 is a diagram illustrating an example of display of a matrix and images by the display controlling function according to the first embodiment.

FIG. 22 is a diagram illustrating an example of display of a matrix and images by the display controlling function 15e according to the first embodiment. For example, as illustrated in FIG. 22, the display controlling function 15e displays the selected matrix 80 on the display 10. Although not illustrated in FIG. 22, when displayed, the selected matrix 80 additionally includes cells representing classifications of the kind of a gyrus having a hierarchical structure as illustrated in FIG. 21.

The display controlling function 15e also displays an image of the whole brain as a reference image. For example, the display controlling function 15e displays a magnetization prepared rapid gradient echo (MP-RAGE) image 91 of the whole brain, a Q-ball imaging (QBI) image 92 of the whole brain, and a T2 weighted image 93 of the whole brain. The image displayed as a reference image is not limited to the MP-RAGE image, the QBI image, and the T2 W image. For example, the display controlling function 15e may display, as a reference image, an image specified by the operator.

Then, the display controlling function 15e receives, from the operator through the input circuitry 9, an operation to select a cell of a gyrus or a cell of a white matter region included in the matrix 80. Then, when a cell of a gyrus arranged along the horizontal axis in the matrix 80 is selected, the display controlling function 15e displays a zoomed image of the selected gyrus. For example, as illustrated in FIG. 22, when cell "g8" arranged on the horizontal axis in the matrix 80 is selected, the display controlling function 15e displays the zoomed MPR image 94 of a gyrus represented by cell "g8".

In addition, the display controlling function 15e displays a zoomed image of a white matter region connected with a gyrus represented by the selected cell, simultaneously with display of the image of the selected gyrus. For example, as illustrated in FIG. 22, when cell "g8" arranged on the horizontal axis in the matrix 80 is selected, the display controlling function 15e displays DTT images 95 and 96 of fiber-clusters contained in two white matter regions connected with the gyrus represented by cell "g8".

In addition, the display controlling function 15e displays a zoom image of a gyrus connected with the selected gyrus simultaneously with display of an image of the selected gyrus. For example, as illustrated in FIG. 22, when cell "g8" arranged on the horizontal axis in the matrix 80 is selected, the display controlling function 15e displays a zoomed MPR image 97 of a gyrus represented by cell "g13" and connected with the gyrus represented by cell "g8", and a zoomed MPR image 98 of a gyrus represented by cell "g14".

FIG. 22 illustrates an example in which the display controlling function 15e arranges the MP-RAGE image 91 of the whole brain, the QBI image 92 of the whole brain, the T2 W image 93 of the whole brain, the MPR image 94, the DTT images 95 and 96, and the MPR images 97 and 98, and displays the arrangement. However, the method of displaying the images is not limited thereto. For example, the display controlling function 15e may switch and display the images in accordance with an instruction from the operator.

The display controlling function 15e may display the MPR images 94, 97, and 98 of a predetermined section among three mutually orthogonal sections of an axial section, a sagittal section, and a coronal section, or may display the images of a section specified by the operator.

In addition, the display controlling function 15e displays, on the display 10, an image illustrating a plurality of brain functional localized regions, and highlights a specific brain functional localized region among a plurality of brain functional localized regions arrayed in the matrix 80 in accordance with an operation to select the specific brain functional localized region from among brain functional localized regions displayed on this image. For example, the display controlling function 15e displays a three dimensional image 99 indicating a region of a gyrus connected with a selected gyrus simultaneously with display of an image of the selected gyrus.

Figure 23:
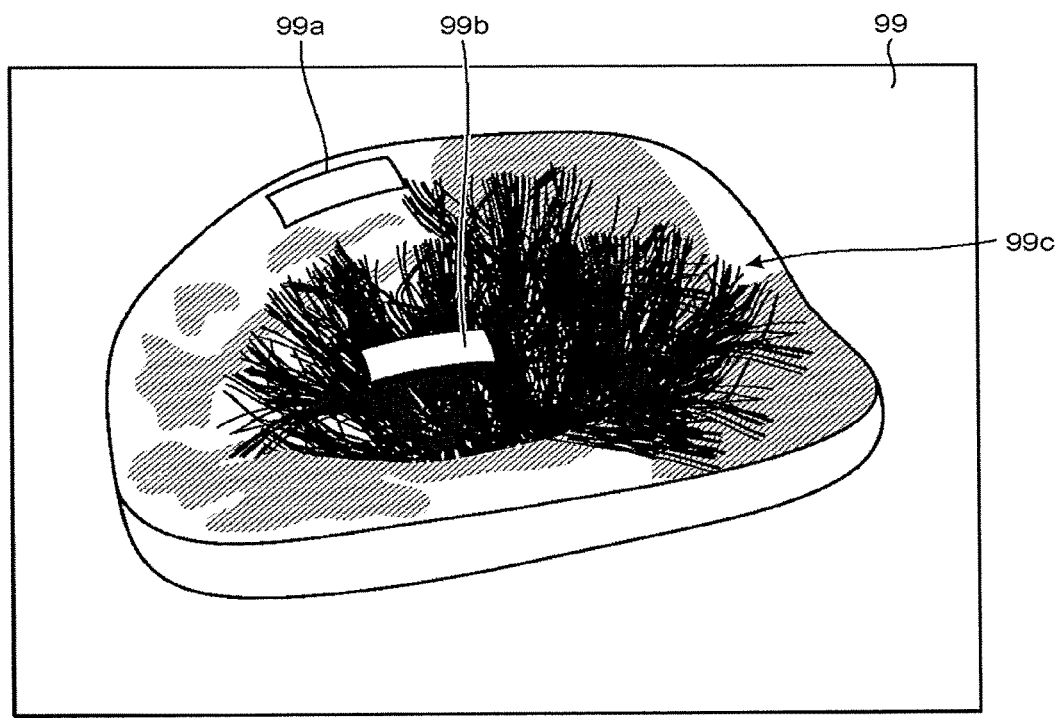
FIG. 23 is a diagram illustrating an exemplary three-dimensional image displayed by the display controlling function according to the first embodiment.

FIG. 23 is a diagram illustrating an exemplary three dimensional image displayed by the display controlling function 15e according to the first embodiment. For example, as illustrated in FIG. 23, the display controlling function 15e displays the three dimensional image 99 of the brain generated by, for example, volume rendering. Then, the display controlling function 15e displays, on the three dimensional image 99, a region 99a indicating gyrus "g13" connected with selected gyrus "g8" and a region 99b indicating gyrus "g14". The display controlling function 15e also displays, on the three dimensional image 99, a DTT image 99c illustrating a fiber-cluster contained in a white matter region connected with selected gyrus "g8".

The display controlling function 15e receives, from the operator through the input circuitry 9, an operation to select a specific region from among regions of gyri displayed on the three dimensional image 99. Then, when a region of a gyrus is selected on the three dimensional image 99, the display controlling function 15e highlights a cell of a gyrus corresponding to the selected region in the matrix 80.

The display controlling function 15e receives, from the operator through the input circuitry 9, an operation to select a specific fiber-cluster from among fiber-clusters displayed on the three dimensional image 99. Then, when the fiber-cluster is selected on the three dimensional image 99, the display controlling function 15e highlights a cell of a white matter region corresponding to the selected fiber-cluster in the matrix 80.

The above describes the processing functions of the processing circuitry 15. For example, each processing function described above is stored as a computer-executable program in the memory circuitry 11. The processing circuitry 15 achieves the processing function corresponding to each program by reading out the program from the memory circuitry 11 and executing the read program. In other words, having read out the programs, the processing circuitry 15 has the processing functions illustrated in FIG. 1.

Although FIG. 1 illustrates the example in which each processing function is achieved by the single processing circuitry 15, the embodiments are not limited thereto. For example, the processing circuitry 15 may be configured as a combination of a plurality of independent processors and may achieve each processing function through each processor executing a corresponding program. The processing functions of the processing circuitry 15 may be distributed or integrated to a single processing circuit or a plurality of processing circuits.

Figure 24:
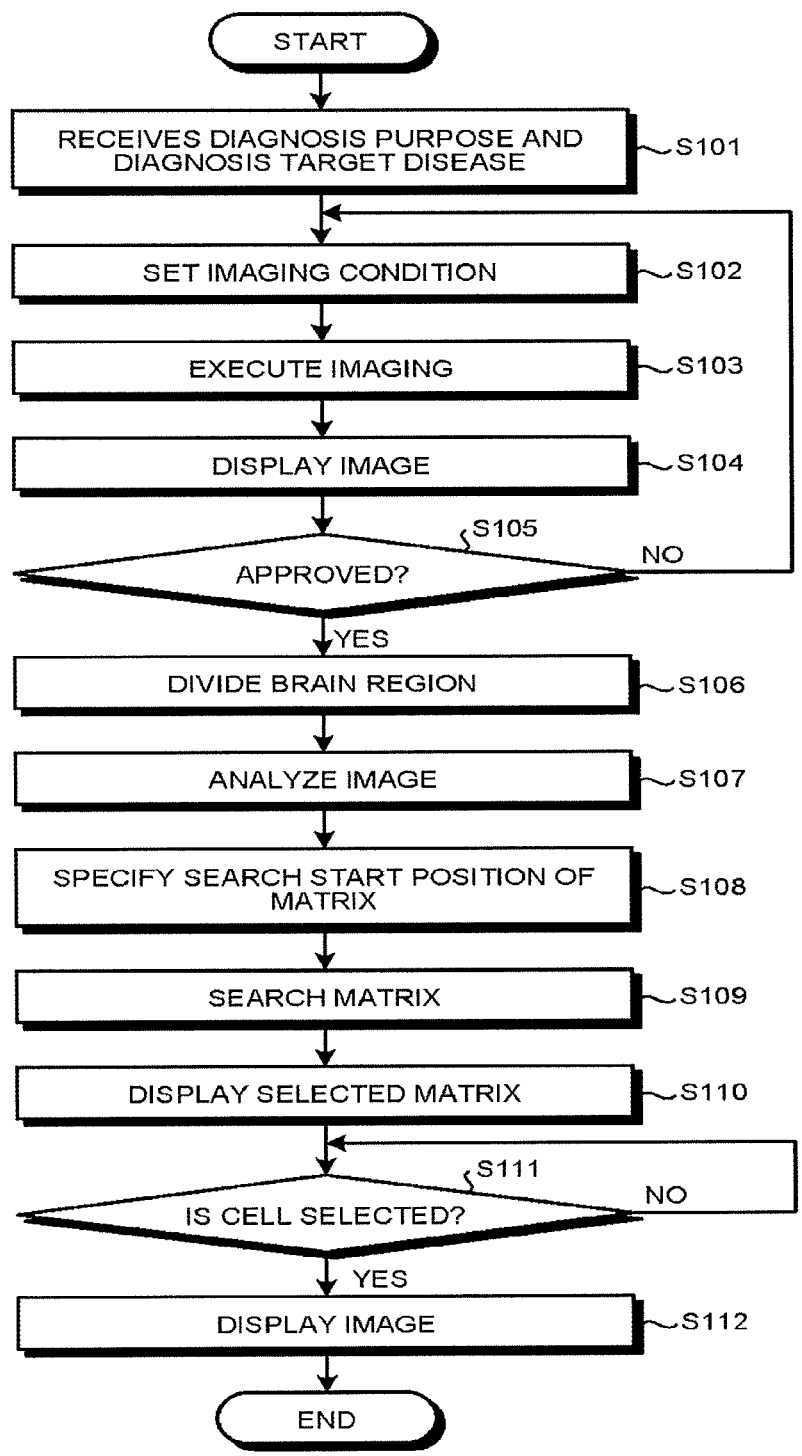
FIG. 24 is a flowchart illustrating a process of processing performed by the MRI apparatus according to the first embodiment.

FIG. 24 is a flowchart illustrating a process of processing performed by the MRI apparatus 100 according to the first embodiment. For example, as illustrated in FIG. 24, the setting function 15a in the MRI apparatus 100 according to the present embodiment first receives a diagnosis purpose and a diagnosis target disease from the operator (step S101). The setting function 15a sets an imaging condition to collect an analysis target image determined in advance for the diagnosis purpose and the disease (step S102).

Thereafter, the executing function 13a and the image generating function 14a execute imaging (step S103). Specifically, the executing function 13a collects MR signal data for generating the analysis target image based on sequence execution data generated by the setting function 15a. The image generating function 14a generates the analysis target image based on the collected MR signal data.

Subsequently, the analyzing function 15b displays the analysis target image generated by the image generating function 14a on the display 10 (step S104). This allows the operator to check whether the generated image is relevant as an analysis target.

Having received an input to deny the analysis target image from the operator through the input circuitry 9 (No at step S105), the analyzing function 15b controls the setting function 15a to reset the imaging condition. Specifically, for example, the setting function 15a receives an operation to reset the imaging condition from the operator, and re-executes imaging through the executing function 13a and the image generating function 14a based on the reset imaging condition. Then, the analyzing function 15b re-displays an acquired image as the analysis target image on the display 10.

Then, having received an input to approve the analysis target image from the operator through the input circuitry 9 (Yes at step S105), the analyzing function 15b performs an image analysis of the analysis target image. The analyzing function 15b first divides a brain region included in the analysis target image into a plurality of brain functional localized regions (step S106). Thereafter, the analyzing function 15b performs the texture analysis on each localized region, and analyzes a difference in a predetermined parameter from the normal brain (step S107).

Subsequently, the specifying function 15c specifies a search start position of a matrix (step S108). Specifically, the specifying function 15c specifies the search start position for the AFM, the CFM, and the PFM using the DSAM. The specifying function 15c specifies the search start position using the DSAM for the definitive diagnosis if the diagnosis purpose received from the operator is the definitive diagnosis, or specifies the search start position using the DSAM for the screening if the diagnosis purpose received from the operator is the screening.

Subsequently, the searching function 15d searches the matrix using the specified search start position (step S109). Specifically, the searching function 15d searches each of the AFM, the CFM, and the PFM using the search start position specified by the specifying function 15c.

Subsequently, the display controlling function 15e displays a matrix of selected brain functional localized regions (step S110). Then, if a cell in the matrix is selected by the operator (Yes at step S111), the display controlling function 15e displays an image corresponding to the selected cell on the display 10 (step S112).

As described above, in the present embodiment, after the likelihood of an abnormality candidate region is specified from the DSAM based on a result of an image analysis, a fiber-cluster and a gyrus as abnormality candidate regions related to the abnormality candidate region are searched, and a result of the search is displayed.

Steps S101 and S102 among the steps described above are achieved by, for example, the processing circuitry 15 calling a predetermined program corresponding to the setting function 15a from the memory circuitry 11 and executing the program. Step S103 is achieved by, for example, the processing circuitry 13 calling a predetermined program corresponding to the executing function 13a from the memory circuitry 11 and executing the program, and the processing circuitry 14 calling a predetermined program corresponding to the image generating function 14a from the memory circuitry 11 and executing the program.

Steps S104 to S107 are achieved by, for example, the processing circuitry 15 calling a predetermined program corresponding to the analyzing function 15b from the memory circuitry 11 and executing the program. Step S108 is achieved by, for example, the processing circuitry 15 calling a predetermined program corresponding to the specifying function 15c from the memory circuitry 11 and executing the program. Step S109 is achieved by, for example, the processing circuitry 15 calling a predetermined program corresponding to the searching function 15d from the memory circuitry 11 and executing the program. Steps S110 to S112 are achieved by, for example, the processing circuitry 15 calling a predetermined program corresponding to the display controlling function 15e from the memory circuitry 11 and executing the program.

According to the first embodiment as described above, classification of fiber-clusters as connection paths between brain functional localized regions and between these brain functional localized regions and organ systems based on their functions produces a matrix (the AFM, the CFM, or the PFM) in which cortex regions are arranged separately from white matter regions as disordered regions to be diagnosed. The classification also produces a matrix (the DSAM) in which a predilection site of a lesion of each brain disease and a value indicating this predilection degree are set for each of brain functional localized regions of cortex regions and white matter regions. The produced DSAM has different contents between the definitive diagnosis and the screening.

After a matrix is set in accordance with a diagnosis purpose, a brain region included in an image of the subject is divided into a plurality of brain functional localized regions, and an image of each region is analyzed. Then, an analysis value obtained by the analysis and the DSAM are referred to determine the priority of a region that requires attention. Relevant gyri and white matter regions are specified from the AFM, the CFM, the PFM, and image analysis and diagnose determination are carried out. Images obtained by imaging the subject are accumulated and compared to images of a normal brain tissue to sequentially update a value related to a predilection site in the DSAM, improving the accuracy of the value.

The configuration above can provide a framework that is easily understandable by a general neuroradiologist or physician and uses information on brain functional localized regions and their inter-regional connectivity therebetween in accordance with a diagnosis purpose. This results in improved diagnostic performance of a general neuroradiologist or physician, thereby achieving efficient detection of an abnormality site in units of brain functional localized regions.

In the first embodiment, a matrix is presented in which cortex regions are separated from white matter regions as disordered regions to be diagnosed in a fiber-cluster classified based on its function. In the matrix, only a region having a high attention degree in the DSAM is selectively displayed.

Accordingly, a mechanism related to the framework, which is easily understandable by a general neuroradiologist or physician and uses information on brain functional localized regions and their inter-regional connectivity therebetween in accordance with a diagnosis purpose, can present its diagnose information in an easily understandable manner. This results in improved diagnostic performance of a general neuroradiologist or physician, thereby achieving efficient search and interpretation of an abnormality site in units of brain functional localized regions.

If an image analysis is performed in units of brain functional localized regions, segmentalization of brain functional localized regions would take time for the image analysis. The MRI apparatus 100 according to the first embodiment, however, displays an analysis result using a matrix that is prepared in advance and represents inter-regional connectivity between brain functional localized regions, thereby presenting the analysis result in real time.

The real time in the description above means an effective real time. In other words, the real time means an extremely short time taken to present an analysis result after acquiring an image. For example, when imaging of a patient is continuously performed in a clinical situation, the real time means a time in which the patient remains in the examination room after the imaging, and this does not necessarily mean the time is zero.

According to the first embodiment described above, an image analysis on a plurality of regions in a brain can be supported.

The method of displaying the selected matrix 80 in the first embodiment described above may be changed as appropriate. For example, the display controlling function 15e may further display, on the matrix 80, an analysis value of an image related to each of a plurality of brain functional localized regions.

Figure 25:
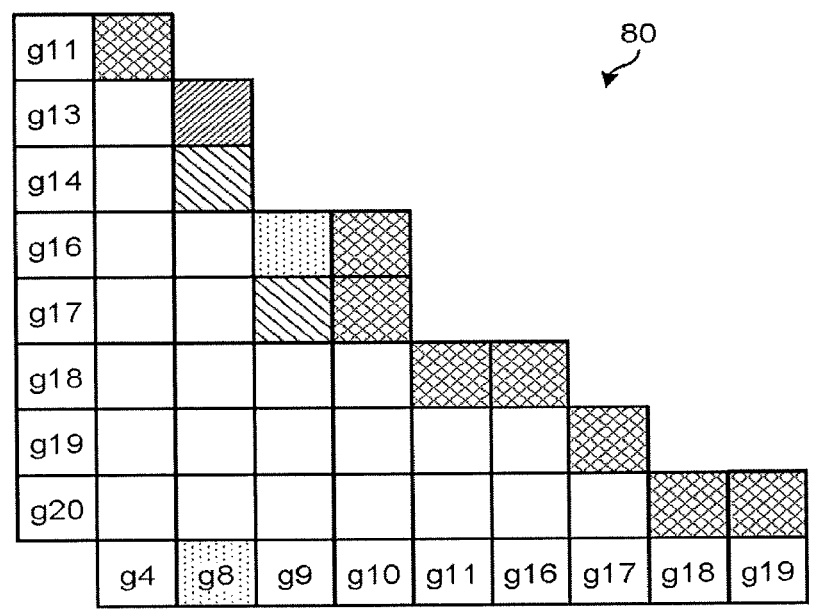
FIG. 25 is a diagram illustrating another example of display of a matrix related to the display controlling function according to the first embodiment.
Figure 26:
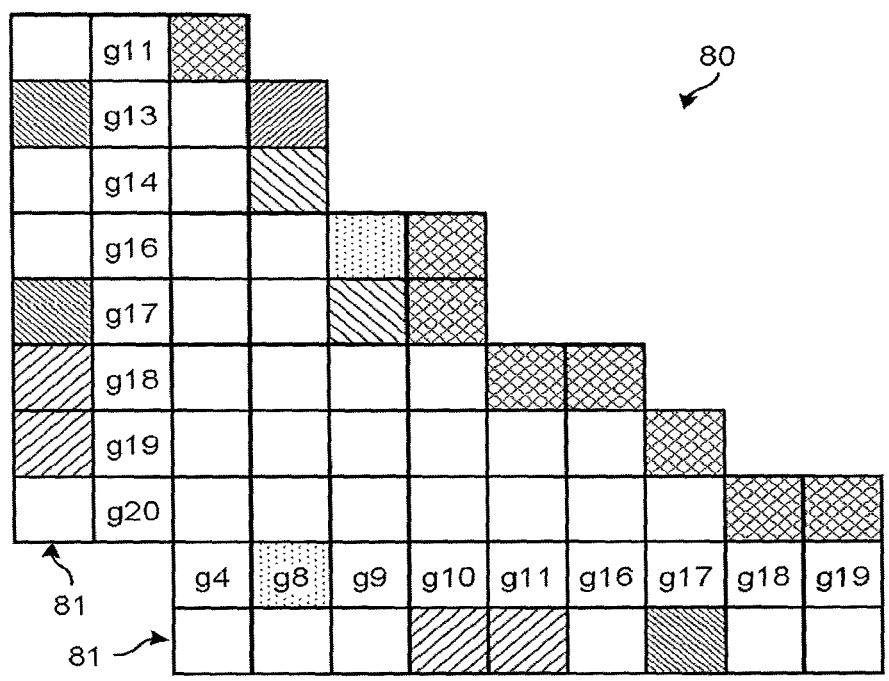
FIG. 26 is a diagram illustrating another example of display of a matrix related to the display controlling function according to the first embodiment.
Figure 27:
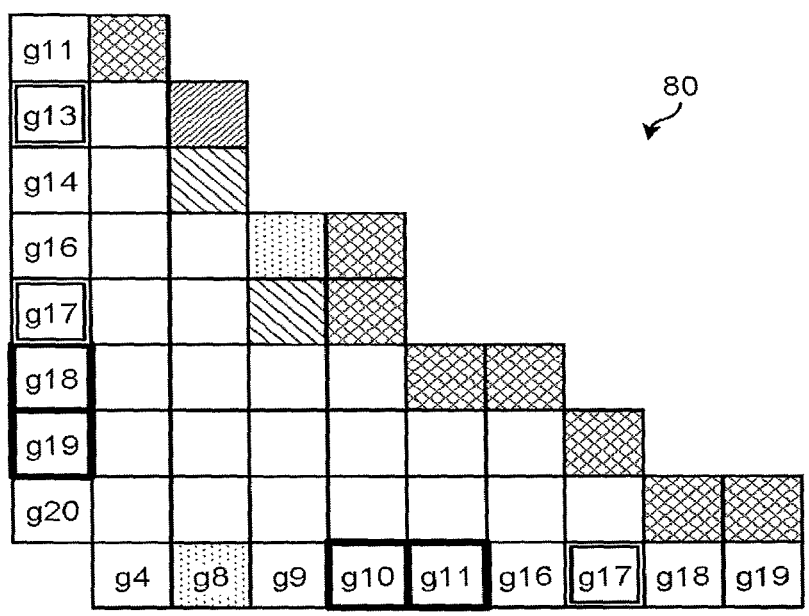
FIG. 27 is a diagram illustrating another example of display of a matrix related to the display controlling function according to the first embodiment.

FIGS. 25 to 27 are diagrams illustrating other examples of display of the matrix 80 related to the display controlling function 15e according to the first embodiment. For example, as illustrated in FIG. 25, the display controlling function 15e allocates different colors to analysis values obtained through an image analysis performed by the analyzing function 15b in accordance with the magnitudes of the analysis values. Then, the display controlling function 15e displays the matrix 80 with a cell of a white matter region as an element of the matrix and a cell of a gyrus as an axial element of the matrix in colors in accordance with the analysis values.

In this case, the display controlling function 15e switches the analysis values displayed on the matrix 80 depending on the kind of an analysis target image. For example, the display controlling function 15e receives an operation to select the kind of an analysis value from the operator through the input circuitry 9. Then, the display controlling function 15e switches display of the matrix 80 based on an analysis result of an image corresponding to the analysis value selected by the operator.

In the description above, a cell of a white matter region and a cell of a gyrus are displayed in colors in accordance with analysis values, but the method of displaying the analysis values is not limited thereto. For example, cells may be displayed in a gray scale with different intensities in accordance with analysis values, or may be displayed in different patterns in accordance with analysis values.

For example, the display controlling function 15e may further display, on the matrix 80, efferent or afferent information obtained from the PFM. For example, as illustrated in FIG. 26, the display controlling function 15e further displays a cell 81 for displaying an efferent or afferent type near a cell of a gyrus as an axial element of the matrix 80. Then, the display controlling function 15e displays the cell 81 near a gyrus connected with an efferent fiber-cluster, and the cell 81 near a gyrus connected with an afferent fiber-cluster, in different colors. Alternatively, for example, as illustrated in FIG. 27, the display controlling function 15e may display the border of a cell of a gyrus connected with an efferent fiber-cluster, and the border of a cell of a gyrus connected with an afferent fiber-cluster, in different colors.

In the first embodiment described above, the display controlling function 15e may further display information indicating an organ system obtained from the PFM. For example, the display controlling function 15e displays, in addition to the selected matrix 80 on the display 10, information indicating an organ system detected from the PFM by the searching function 15d.

Figure 28:
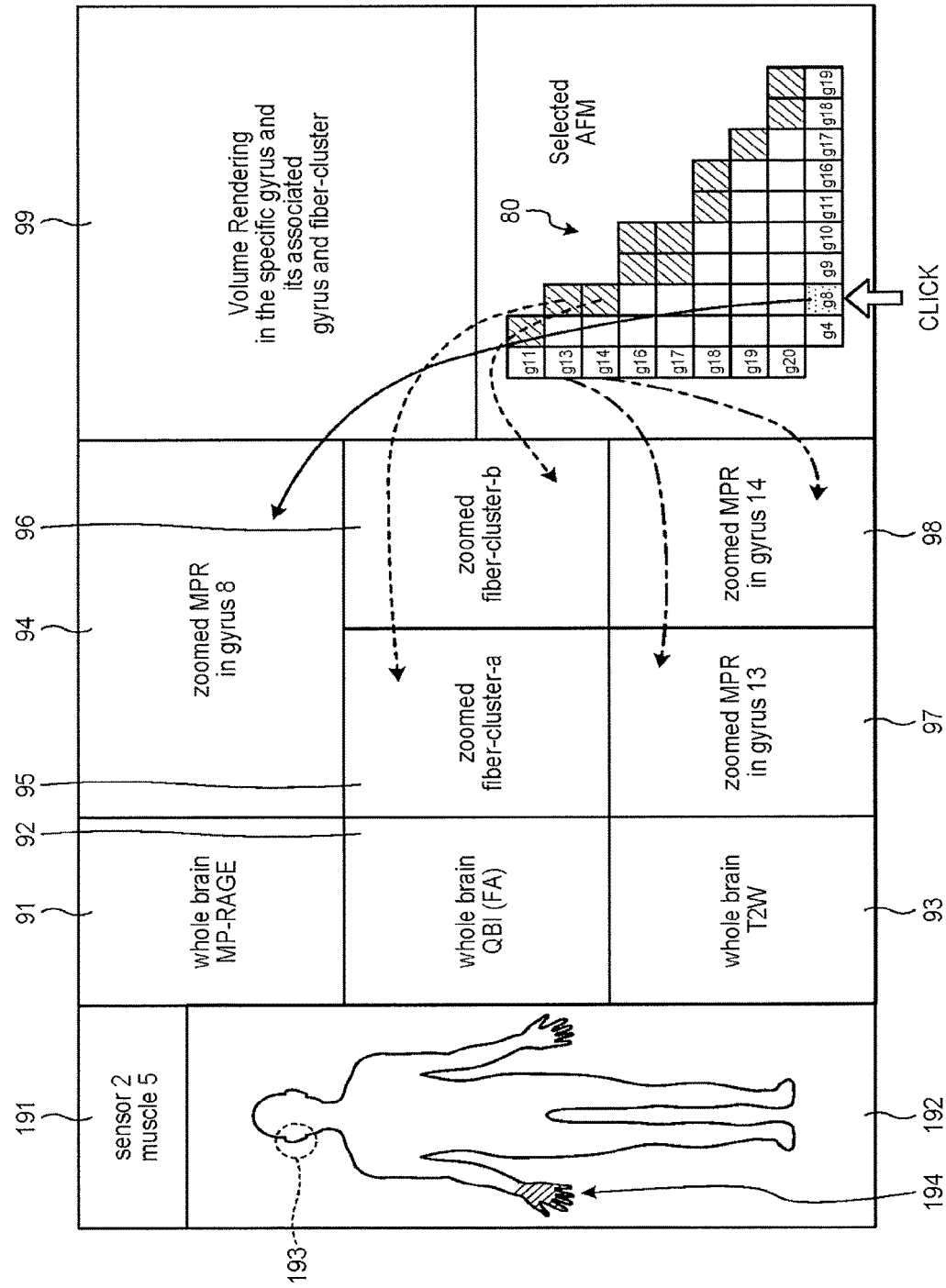
FIG. 28 is a diagram illustrating another example of display of a matrix and an image by the display controlling function according to the first embodiment.

FIG. 28 is a diagram illustrating another example of display of a matrix and an image by the display controlling function 15e according to the first embodiment. For example, as illustrated in FIG. 28, the display controlling function 15e displays, in addition to the matrix 80 and the images illustrated in FIG. 22 on the display 10, information 191 and 192 indicating organ systems detected from the PFM by the searching function 15d. Only one of the information 191 and 192 indicating organ systems may be displayed.

For example, the display controlling function 15e displays, as the information 191 indicating an organ system, text information such as "sensor2" and "muscle5" indicating the kind of a sensory apparatus and the kind of a locomotor apparatus. For example, the display controlling function 15e displays, as the information 192 indicating an organ system, a model image illustrating a body shape of the subject, and displays part of this model image corresponding to an organ system detected by the searching function 15d in an identifiable manner. For example, the display controlling function 15e displays a graphic 193 indicating the position of this part on the model image, or displays a part 194 on the model image corresponding to this part in a display format (for example, a color and a pattern) different from those of other parts.

Second Embodiment

The first embodiment described above describes the example in which the display controlling function 15e displays a matrix of selected brain functional localized regions as a search result of the AFM, the CFM, or the PFM. The present embodiment is, however, not limited thereto. For example, the display controlling function 15e may display a matrix of selected brain functional localized regions based on the DSAM prepared in advance depending on predetermined medical information. The following describes a second embodiment as such an example.

Figure 29:
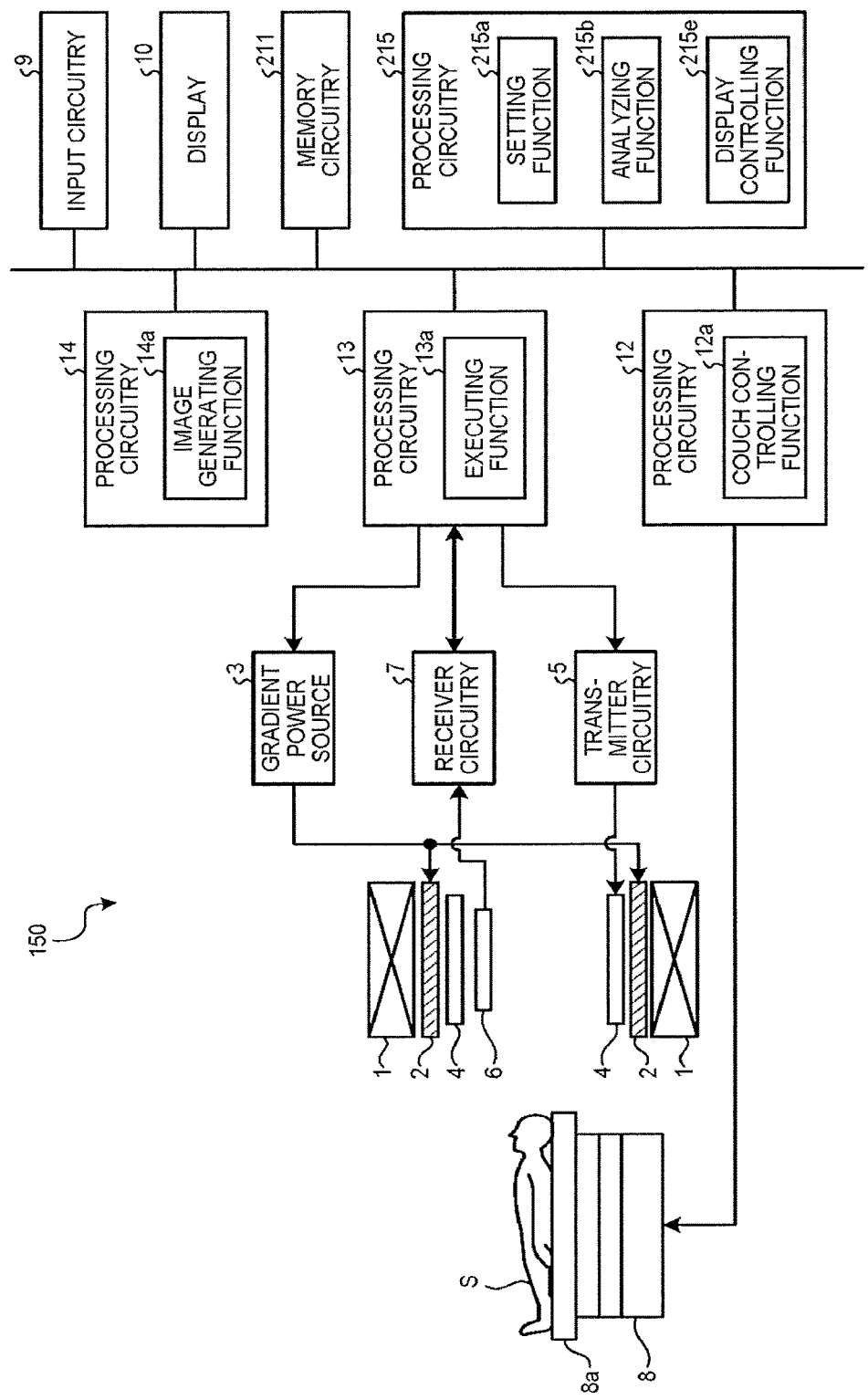
FIG. 29 is a diagram illustrating an exemplary configuration of an MRI apparatus according to a second embodiment.

FIG. 29 is a diagram illustrating an exemplary configuration of an MRI apparatus 150 according to the second embodiment. For example, as illustrated in FIG. 29, the MRI apparatus 150 includes the static magnetic magnet 1, the gradient coil 2, the gradient power source 3, the transmitter coil 4, the transmitter circuitry 5, the receiver coil 6, the receiver circuitry 7, the couch 8, the input circuitry 9, the display 10, memory circuitry 211, the processing circuitry 12, the processing circuitry 13, the processing circuitry 14, and processing circuitry 215.

The present embodiment mainly describes any difference of the configuration of the MRI apparatus 150 from the configuration of the MRI apparatus 100 according to the first embodiment. Any component having the same functionality with that of a component illustrated in FIG. 1 will be denoted by the same reference numeral, and detailed description thereof will be omitted.

With such a configuration, the MRI apparatus 150 according to the present embodiment is used in an image analysis of a brain, which is performed in units of brain functional localized regions.

In the present embodiment, similarly to the memory circuitry 11 described in the first embodiment, the memory circuitry 211 stores therein information on a matrix representing inter-regional connectivity between a plurality of brain functional localized regions. Specifically, similarly to the memory circuitry 11 described in the first embodiment, the memory circuitry 211 stores therein information on the AFM, the CFM, the PFM, and the DSAM.

In the present embodiment, the memory circuitry 211 stores therein information on the DSAM in which an attention degree in accordance with predetermined medical information is set to each of a plurality of brain functional localized regions. The predetermined medical information includes, for example, a neural symptom, a diagnosis purpose, and a disease. The neural symptom includes, for example, specific functions of the brain such as emotion and memory.

For example, the medical information may be a feedback circuitry of the brain. For example, recent studies on diseases such as Alzheimer's disease and Parkinson's disease have discussed a correlation relation between brain functional localized regions likely to suffer a disorder. Such a correlation relation is called a feedback circuitry of the brain. Thus, the DSAM in which an attention degree based on the feedback circuitry is set may be used.

In other words, the MRI apparatus 150 according to the present embodiment is used not only in a diagnosis but also in a study, for example.

In the present embodiment, the processing circuitry 215 has a setting function 215a, an analyzing function 215b, and a display controlling function 215e. The processing circuitry 215 is an exemplary processing circuitry in the claims.

The setting function 215a receives the medical information from the operator. Specifically, the setting function 215a receives an operation to specify the medical information from the operator through the input circuitry 9. For example, the setting function 215a receives, as the medical information, a neural symptom, a diagnosis purpose, a disease, and the kind of the feedback circuitry.

Then, if the medical information is specified by the operator, the setting function 215a sets an imaging condition to collect an analysis target image determined in advance in accordance with the medical information. The setting function 215a generates sequence execution data for collecting the analysis target image based on the set imaging condition, and transmits the generated sequence execution data to the processing circuitry 13. In this manner, the executing function 13a of the processing circuitry 13 collects MR signal data for generating the analysis target image. The image generating function 14a of the processing circuitry 14 generates the analysis target image based on the collected MR signal data.

The analyzing function 215b divides a brain region included in an image of the subject into a plurality of brain functional localized regions, and performs the texture analysis on each localized region. The analyzing function 215b analyzes a difference in a predetermined parameter from the normal brain for each localized region. Processing performed by the analyzing function 215b is the same as the processing performed by the analyzing function 15b as described in the first embodiment, and thus detailed description will be omitted.

The display controlling function 215e selectively displays part of a plurality of brain functional localized regions arranged along the horizontal axis in a matrix based on an attention degree set to each of the brain functional localized regions. Specifically, the display controlling function 215e displays, on the display 10, a matrix in which information indicating part of the brain functional localized regions is arranged along the horizontal axis, and information indicating brain functional localized regions having connectivity with the part of the brain functional localized regions arranged along the horizontal axis is arranged along the vertical axis.

In the present embodiment, the display controlling function 215e displays a matrix of a plurality of selected brain functional localized regions based on attention degrees set to the DSAM. Specifically, the display controlling function 215e displays a matrix in which a gyrus having an attention degree of "2" or larger in the DSAM is arranged along the horizontal axis among a plurality of gyri and fiber-clusters arranged along the horizontal axis in the AFM, the CFM, or the PFM. The display controlling function 215e arranges, along the vertical axis, white matter regions and gyri connected with gyri arranged along the horizontal axis in the AFM, the CFM, or the PFM.

In this manner, the selected matrix 80 is displayed as illustrated in, for example, FIGS. 20 to 22. In the present embodiment, the display controlling function 215e may further display, on the matrix 80, an analysis value of an image related to each of a plurality of brain functional localized regions as illustrated in FIGS. 25 to 27.

Figure 30:
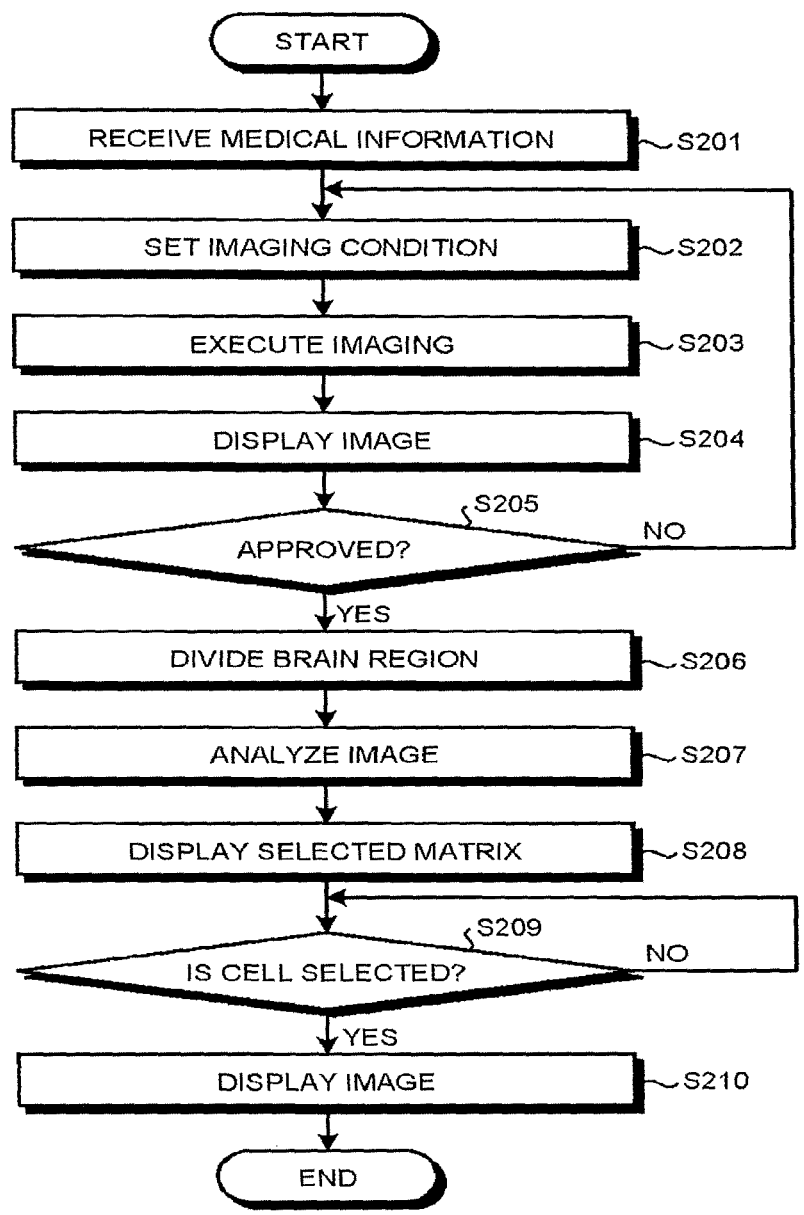
FIG. 30 is a flowchart illustrating a process of processing performed by the MRI apparatus according to the second embodiment.

FIG. 30 is a flowchart illustrating a process of processing performed by the MRI apparatus 150 according to the second embodiment. For example, as illustrated in FIG. 30, in the MRI apparatus 100 according to the present embodiment, first, the setting function 215a receives medical information from the operator (step S201). The setting function 215a sets an imaging condition to collect an analysis target image determined in advance depending on medical information (step S202).

Thereafter, the executing function 13a and the image generating function 14a execute imaging (step S203). Specifically, the executing function 13a collects MR signal data for generating the analysis target image based on sequence execution data generated by the setting function 15a. The image generating function 14a generates the analysis target image based on the collected MR signal data.

Subsequently, the analyzing function 215b displays the analysis target image generated by the image generating function 14a on the display 10 (step S204). This allows the operator to check whether the generated image is relevant as an analysis target.

Having received an input to deny the analysis target image from the operator through the input circuitry 9 (No at step S205), the analyzing function 215b controls the setting function 215a to reset the imaging condition. Specifically, for example, the setting function 215a receives an operation to reset the imaging condition from the operator, and re-executes imaging through the executing function 13a and the image generating function 14a based on the reset imaging condition. Then, the analyzing function 215b re-displays an acquired image as the analysis target image on the display 10.

Having received an input to approve the analysis target image from the operator through the input circuitry 9 (Yes at step S205), the analyzing function 215b performs an image analysis of the analysis target image. First, the analyzing function 215b divides a brain region included in the analysis target image into a plurality of brain functional localized regions (step S206). Thereafter, the analyzing function 215b performs the texture analysis on each localized region, and analyzes a difference in a predetermined parameter from the normal brain (step S207).

Subsequently, the display controlling function 215e displays a matrix of a plurality of selected brain functional localized regions based on attention degrees set to the DSAM, (step S208). Then, if a cell of the matrix is selected by the operator (Yes at step S209), the display controlling function 215e displays an image corresponding to the selected cell on the display 10 (step S210).

Steps S201 and S202 among the steps described above is achieved by, for example, the processing circuitry 215 calling a predetermined program corresponding to the setting function 215a from the memory circuitry 211 and executing the program. Step S203 is achieved by, for example, the processing circuitry 13 calling a predetermined program corresponding to the executing function 13a from the memory circuitry 211 and executing the program, and the processing circuitry 14 calling a predetermined program corresponding to the image generating function 14a from the memory circuitry 211 and executing the program.

Steps S204 to S207 are achieved by, for example, the processing circuitry 215 calling a predetermined program corresponding to the analyzing function 215b from the memory circuitry 211 and executing the program. Steps S208 to S210 are achieved by, for example, the processing circuitry 215 calling a predetermined program corresponding to the display controlling function 215e from the memory circuitry 211 and executing the program.

As described above, in the second embodiment, a matrix of selected brain functional localized regions is displayed using the DSAM prepared in accordance with medical information such as a neural symptom, a diagnosis purpose, a disease, and the kind of a feedback circuitry.

Accordingly, a mechanism related to a framework that is easily understandable by the operator and uses information on brain functional localized regions and their inter-regional connectivity therebetween in accordance with, for example, a study purpose as well as a diagnosis purpose can present its diagnose information in an easily understandable manner. This results in efficient search and interpretation of an abnormality site in units of brain functional localized regions.

Thus, according to the second embodiment, an image analysis on a plurality of regions in a brain can be supported.

Although the first and second embodiments above describe embodiments of an MRI apparatus, the embodiments are not limited thereto. For example, the technology disclosed in the subject application is applicable to an image processing apparatus. The following describes a third embodiment as an example in which the technology described in the first embodiment is applied to an image processing apparatus, and describes a fourth embodiment as an example in which the technology described in the second embodiment is applied to an image processing apparatus.

Third Embodiment

Figure 31:
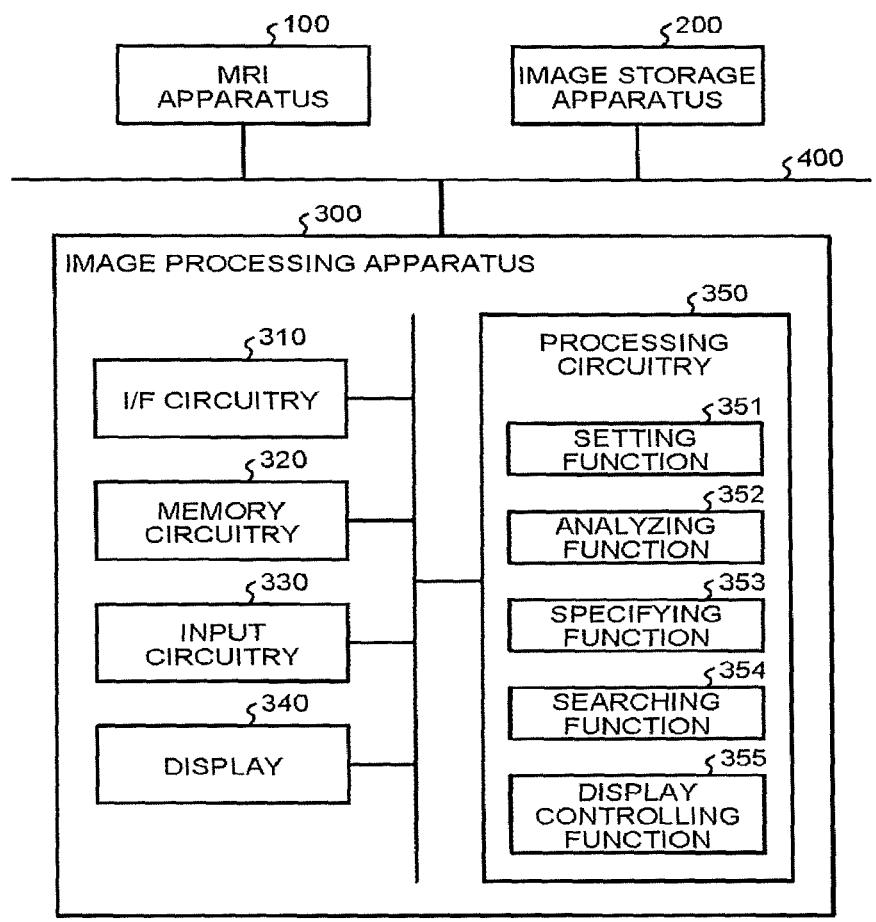
FIG. 31 is a diagram illustrating an exemplary configuration of an image processing apparatus according to a third embodiment.

FIG. 31 is a diagram illustrating a configuration example of an image processing apparatus 300 according to a third embodiment. For example, as illustrated in FIG. 31, the image processing apparatus 300 according to the present embodiment is connected to the MRI apparatus 100 and an image storage apparatus 200 through a network 400.

The MRI apparatus 100 collects image data on a subject by utilizing the magnetic resonance phenomenon. Specifically, the MRI apparatus 100 executes various kinds of imaging sequences based on imaging conditions set by an operator of the MRI apparatus 100, thereby collecting magnetic resonance data from the subject. Then, the MRI apparatus 100 subjects the collected magnetic resonance data to image processing such as the Fourier transform to generate two-dimensional or three-dimensional image data.

The image storage apparatus 200 stores therein image data collected by various kinds of image diagnostic apparatus. Specifically, the image storage apparatus 200 acquires image data from the MRI apparatus 100 through the network 400, and stores the acquired image data in memory circuitry provided inside or outside the image storage apparatus 200. For example, the image storage apparatus 200 is implemented by computer equipment such as a server apparatus.

The image processing apparatus 300 processes image data collected by various kinds of image diagnostic apparatus. Specifically, the image processing apparatus 300 acquires image data from the MRI apparatus 100 or the image storage apparatus 200 through the network 400, and stores the acquired image data in memory circuitry provided inside or outside the image processing apparatus 300. The image processing apparatus 300 subjects the acquired image data to various kinds of image processing, and displays the image data before or after the image processing on a display or other similar devices. For example, the image processing apparatus 300 is implemented by computer equipment such as a workstation.

For example, as illustrated in FIG. 31, the image processing apparatus 300 includes an interface (I/F) circuitry 310, memory circuitry 320, input circuitry 330, a display 340, and processing circuitry 350.

The I/F circuitry 310 controls transmitter and communication of various kinds of data to be transmitted and received between the image processing apparatus 300 and other apparatus connected through the network 400. Specifically, the I/F circuitry 310 is connected to the processing circuitry 350, and converts image data output from the processing circuitry 350 into a format compliant with a predetermined communication protocol and transmits the resultant image data to the MRI apparatus 100 or the image storage apparatus 200. The I/F circuitry 310 outputs image data received from the MRI apparatus 100 or the image storage apparatus 200 to the processing circuitry 350. For example, the I/F circuitry 310 is implemented by a network card, a network adapter, or a network interface controller (NIC).

The memory circuitry 320 stores therein various kinds of data. Specifically, the memory circuitry 320 is connected to the processing circuitry 350, and the memory circuitry 320 stores therein input image data or outputs stored image data to the processing circuitry 350 in response to a command transmitted from the processing circuitry 350. For example, the memory circuitry 320 is implemented by a semiconductor memory device, such as a random access memory (RAM) and a flash memory, a hard disk, or an optical disc.

The input circuitry 330 receives an input operation of various kinds of instructions and various kinds of information from the operator. Specifically, the input circuitry 330 is connected to the processing circuitry 350, and converts an input operation received from the operator into an electric signal and outputs the resultant signal to the processing circuitry 350. For example, the input circuitry 330 is implemented by a trackball, a switch button, a mouse, a keyboard, or a touch panel.

The display 340 displays various kinds of information and various kinds of images. Specifically, the display 340 is connected to the processing circuitry 350, and displays images in various kinds of formats based on image data output from the processing circuitry 350. For example, the display 340 is implemented by a liquid crystal monitor, a cathode ray tube (CRT) monitor, or a touch panel.

The processing circuitry 350 controls each component included in the image processing apparatus 300 based on an input operation received from the operator through the input circuitry 330. Specifically, the processing circuitry 350 controls the memory circuitry 320 to store therein image data output from the I/F circuitry 310. The processing circuitry 350 controls the display 340 to display image data read from the memory circuitry 320. For example, the processing circuitry 350 is implemented by a processor.

With such a configuration, the image processing apparatus 300 according to the present embodiment is used in, for example, an image analysis of the brain, which is performed in units of brain functional localized regions.

In the present embodiment, similarly to the memory circuitry 11 described in the first embodiment, the memory circuitry 320 stores therein information on a matrix representing inter-regional connectivity between a plurality of brain functional localized regions. Specifically, similarly to the memory circuitry 11 described in the first embodiment, the memory circuitry 320 stores therein information on the AFM, the CFM, the PFM, and the DSAM.

The processing circuitry 350 has a setting function 351, an analyzing function 352, a specifying function 353, a searching function 354, and a display controlling function 355. The processing circuitry 350 is an exemplary processing circuitry in the claims.

Similarly to the setting function 15a described in the first embodiment, the setting function 351 receives a diagnosis purpose and a diagnosis target disease from the operator.

The analyzing function 352 has the same function as that of the analyzing function 15b described in the first embodiment. Although the analyzing function 15b performs an image analysis using an analysis target image generated by the image generating function 14a in the first embodiment, the analyzing function 352 according to the present embodiment acquires an analysis target image from the MRI apparatus 100 or the image storage apparatus 200 through the network 400, and performs an image analysis.

The specifying function 353 has the same function as that of the specifying function 15c described in the first embodiment. The searching function 354 has the same function as that of the searching function 15d described in the first embodiment. The display controlling function 355 has the same function as that of the display controlling function 15e described in the first embodiment.

In the present embodiment, the input circuitry 330, the display 340, and the memory circuitry 320 further have the functions of the input circuitry 9, the display 10, and the memory circuitry 11 described in the first embodiment.

The above describes the processing functions of the processing circuitry 350. For example, each processing function described above is stored as a computer-executable program in the memory circuitry 320. The processing circuitry 350 reads each computer program from the memory circuitry 320 and executes the read computer program, thereby implementing the processing function corresponding to each computer program. In other words, the processing circuitry 350 that has read each program has each processing function illustrated in FIG. 31.

Note that, in FIG. 31, a description has been given of an example where each processing function is implemented by the single processing circuitry 350, but the embodiments are not limited thereto. For example, the processing circuitry 350 may be formed by a combination of independent processors, and the processing functions may be implemented by each processor executing each computer program. The processing functions included in the processing circuitry 350 may be implemented as being appropriately distributed or integrated in a single or plurality of processing circuits.

Such a configuration can obtain the same effects as those of the first embodiment. Thus, similarly to the first embodiment, according to the third embodiment, an image analysis on a plurality of regions in a brain can be supported.

Fourth Embodiment

Figure 32:
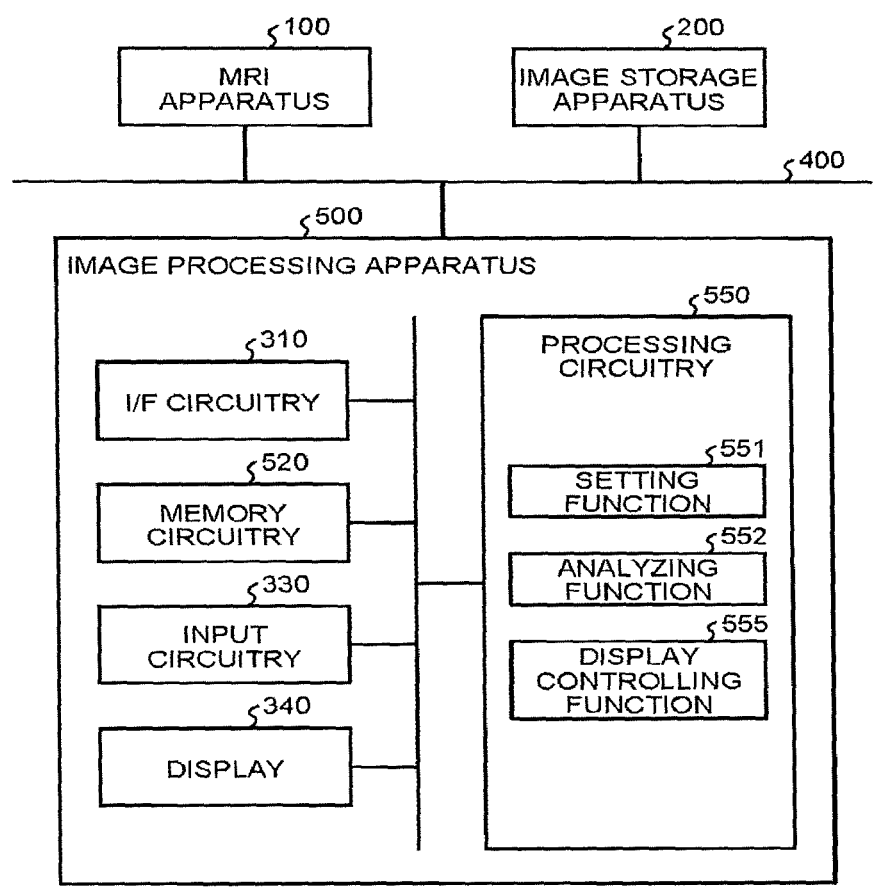
FIG. 32 is a diagram illustrating an exemplary configuration of an image processing apparatus according to a fourth embodiment.

FIG. 32 is a diagram illustrating an exemplary configuration of an image processing apparatus 500 according to the fourth embodiment. For example, as illustrated in FIG. 32, the image processing apparatus 500 according to the present embodiment is connected with the MRI apparatus 100 and the image storage apparatus 200 through the network 400. The MRI apparatus 100 and the image storage apparatus 200 have the same configurations as those illustrated in FIG. 31, and thus description thereof will be omitted.

The image processing apparatus 500 processes image data collected by various kinds of image diagnose apparatuses. Specifically, the image processing apparatus 500 acquires the image data from the MRI apparatus 100 or the image storage apparatus 200 through the network 400, and stores the image data in internally or externally provided memory circuitry. The image processing apparatus 500 performs various kinds of image processing on the acquired image data, and displays the image data before or after the image processing on, for example, a display. For example, the image processing apparatus 500 is achieved by a computer apparatus such as a work station.

For example, as illustrated in FIG. 32, the image processing apparatus 500 includes interface (I/F) circuitry 310, memory circuitry 520, the input circuitry 330, the display 340, and processing circuitry 550.

The present embodiment mainly describes any difference of the configuration of the image processing apparatus 500 from the configuration of the image processing apparatus 300 according to the third embodiment. Any component having the same functionality as that of a component illustrated in FIG. 31 will be denoted by the same reference numeral, and detailed description thereof will be omitted.

With such a configuration, the image processing apparatus 500 according to the present embodiment is used in an image analysis of the brain, which is performed in units of brain functional localized regions.

In the present embodiment, similarly to the memory circuitry 211 described in the second embodiment, the memory circuitry 520 stores therein information on a matrix representing inter-regional connectivity between a plurality of brain functional localized regions. Specifically, similarly to the memory circuitry 211 described in the second embodiment, the memory circuitry 520 stores therein information on the AFM, the CFM, the PFM, and the DSAM.

The processing circuitry 550 has a setting function 551, an analyzing function 552, and a display controlling function 555. The processing circuitry 550 is an exemplary processing circuitry in the claims.

Similarly to the setting function 215a described in the second embodiment, the setting function 551 receives medical information from the operator.

The analyzing function 552 has the same function as that of the analyzing function 215b described in the second embodiment. Although the analyzing function 215b performs an image analysis using an analysis target image generated by the image generating function 14a in the second embodiment, the analyzing function 552 according to the present embodiment acquires an analysis target image from the MRI apparatus 100 or the image storage apparatus 200 through the network 400, and performs an image analysis.

The display controlling function 555 has the same function as that of the display controlling function 215e described in the second embodiment.

A description has been given of each processing function included in the processing circuitry 550. For example, the above-mentioned processing functions are stored in the memory circuitry 520 in the form of computer programs that can be executed by a computer. The processing circuitry 550 reads each computer program from the memory circuitry 520 and executes the read computer program, thereby implementing the processing function corresponding to each computer program. In other words, the processing circuitry 550 that has read each computer program has each processing function illustrated in FIG. 32.

Note that, in FIG. 32, a description has been given of an example where each processing function is implemented by the single processing circuitry 550, but the embodiments are not limited thereto. For example, the processing circuitry 550 may be configured by a combination of independent processors, and each processing function may be implemented by each processor executing each computer program. Each processing function included in the processing circuitry 550 may be implemented in a manner that the processing functions are appropriately distributed or integrated in a single or plurality of processing circuits.

Such a configuration can obtain the same effects as those of the second embodiment. Thus, similarly to the second embodiment, according to the fourth embodiment, an image analysis on a plurality of regions in a brain can be supported.

Although the third and fourth embodiments described above describes the example in which the image processing apparatus displays matrices and images on the display provided thereto, the embodiments are not limited thereto. For example, the image processing apparatus may output matrices and images to an image display apparatus connected through the network 400.

A recent image processing system can have a thin-client configuration in which a client apparatus used by the operator executes minimum necessary part of processing and a server apparatus executes most of the processing. For example, in such an image processing system, the server apparatus may have the function of the image processing apparatus described in the third or fourth embodiment, and the client apparatus may display matrices and images.

The term "processor" used in the above-mentioned embodiments means, for example, a central processing unit (CPU), a graphics processing unit (GPU), or a circuit such as an application specific integrated circuit (ASIC) and a programmable logic device (for example, a simple programmable logic device (SPLD), a complex programmable logic device (CPLD), and a field programmable gate array (FPGA)). A computer program may be directly incorporated in a circuit of the processor instead of storing a computer program in the memory circuitry. In this case, the processor implements its functions by reading and executing the computer programs incorporated in the circuit. Each processor in the present embodiment is not limited to the case where each processor is configured as a single circuit, and a plurality of independent circuits may be combined to configure a single processor so as to implement their functions.

According to at least one of the embodiments described above, an image analysis on a plurality of regions in the brain can be supported.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus, comprising: processing circuitry configured to
    perform control to graphically display, on a display, a matrix, the matrix representing inter-regional connectivity between a plurality of regions in a brain, and including therein a plurality of elements representing the plurality of regions arranged along at least a first axis, and
    perform, based on an attention degree set to each of the plurality of regions, control to selectively and graphically display part of the elements of the regions arranged along the first axis in the matrix.

2. The magnetic resonance imaging apparatus according to claim 1, wherein the processing circuitry is further configured to perform control to display the matrix in which information indicating the part of the elements of the regions is arranged along the first axis and information indicating a region having connectivity with the part of the elements of the regions is arranged along a second axis.

3. The magnetic resonance imaging apparatus according to claim 2, wherein the processing circuitry is further configured to perform control to display the information indicating the region and information indicating a functional or anatomical category to which the region belongs, hierarchically along the first axis and the second axis.

4. The magnetic resonance imaging apparatus according to claim 1, wherein the attention degree is set in accordance with a diagnosis purpose and a disease, or in accordance with a neural symptom.

5. The magnetic resonance imaging apparatus according to claim 1, wherein the processing circuitry is further configured to perform control to display an image of a selected region, in accordance with an operation to select a displayed region.

6. The magnetic resonance imaging apparatus according to claim 5, wherein the processing circuitry is further configured to perform control to display a zoomed image of the selected region.

7. The magnetic resonance imaging apparatus according to claim 1, wherein the processing circuitry is further configured to perform control to display an arrangement of an image of the part of the elements of the regions and an image of a region having connectivity with the part of the elements of the regions.

8. The magnetic resonance imaging apparatus according to claim 1, wherein the processing circuitry is further configured to perform control to display an image illustrating the plurality of regions, and control to highlight a specific region among the plurality of regions arrayed in the matrix, in accordance with an operation to select the specific region from among the regions displayed on the image.

9. The magnetic resonance imaging apparatus according to claim 1, wherein the processing circuitry is further configured to perform control to additionally display an analysis value of an image related to each of the regions on the matrix.

10. The magnetic resonance imaging apparatus according to claim 9, wherein the processing circuitry is further configured to perform control to switch an analysis value displayed on the matrix in accordance with a kind of an analysis target image.

11. An image processing apparatus, comprising:
    processing circuitry configured to
        perform control to graphically display, on a display, a matrix, the matrix representing inter-regional connectivity between a plurality of regions in a brain, and including a plurality of elements representing the plurality of regions arranged along at least a first axis, and
        perform, based on an attention degree set to each of the plurality of regions, control to selectively and graphically display part of the elements of the regions arranged along the first axis in the matrix.

* * * * *